US007135619B1

(12) United States Patent
Visser et al.

(10) Patent No.: US 7,135,619 B1
(45) Date of Patent: Nov. 14, 2006

(54) EXPRESSION IN PLANTS OF STARCH BINDING DOMAINS AND/OR OF PROTEIN-FUSIONS CONTAINING STARCH BINDING DOMAINS

(75) Inventors: Richard Gerardus F. Visser, Bennekom (NL); Jean-Paul Vincken, Renkum (NL)

(73) Assignees: Wageningen Universiteit, Wageningen (NL); Cooperatieve Verkoop-en Productievereniging van Aardappelmeel en Derivaten AVEBE B.A., Foxhol (NL)

( * ) Notice: Subject to any disclaimer, the term of this patent is extended or adjusted under 35 U.S.C. 154(b) by 372 days.

(21) Appl. No.: 10/009,876

(22) PCT Filed: Jun. 11, 1999

(86) PCT No.: PCT/NL00/00406

§ 371 (c)(1),
(2), (4) Date: May 6, 2002

(87) PCT Pub. No.: WO00/77165

PCT Pub. Date: Dec. 21, 2000

(30) Foreign Application Priority Data

Jun. 11, 1999 (EP) .................................. 99201862

(51) Int. Cl.
*C12N 15/52* (2006.01)
*C12N 15/62* (2006.01)
*C12N 15/82* (2006.01)
*A01H 5/00* (2006.01)
*A01H 5/10* (2006.01)

(52) U.S. Cl. ...................... 800/284; 800/288; 800/298; 800/317.2; 800/320; 800/320.1; 435/320.1; 536/23.4

(58) Field of Classification Search ................ 536/23.1, 536/23.2, 23.4, 23.6, 23.7; 800/278, 284, 800/288, 298, 317.2, 320.1, 320; 435/320.1
See application file for complete search history.

(56) References Cited

U.S. PATENT DOCUMENTS

| 5,349,123 A | 9/1994 | Shewmaker et al. |
| 5,750,875 A | 5/1998 | Stalker et al. |
| 6,107,060 A | 8/2000 | Keeling et al. |

FOREIGN PATENT DOCUMENTS

| CA | 2061443 | 8/1993 |
| WO | WO 91/19808 | 12/1991 |
| WO | WO 92/11376 | 7/1992 |
| WO | WO 92/14827 | 9/1992 |
| WO | WO 98/14601 | 4/1998 |
| WO | WO 98/16190 | 4/1998 |
| WO | WO 99/15636 | 4/1999 |

OTHER PUBLICATIONS

Chen et al. Biotechnology Progress, 1991, vol. 7, pp. 225-229.*
Flipse E. et al. Theoretical and Applied Genetics, 1994, vol. 88 pp. 369-375.*
Shah N. et al. Plant Cell and Environment, 1999, vol. 22; pp. 1311-1318; see abstract and p. 1315.*
Dalmia B. et al. Biotechnology and Bioengineering, 1995; vol. 47 pp. 575-584.*
GenBank Accession gi: 142654; Apr. 26, 1993.*
Kortstee A. et al. The Plant Journal, 1996; vol. 10, No. 1; pp. 83-90.*
Chen et al., Improved Adsorption to Starch of a Beta-Galactosidase Fusion Protein Containing the Starch-Binding Domain from *Aspargillus* Glucoamylase. Biotechnology Progress, 7:225-29, 1991.
Dalmia et al, Domain E of *Bacillus macerans* Cyclodextrin Glucanotransferase: An Independent Starch-Binding Domain. Biotechnology and Bioengeneering, 47:575-84, 1995.
Kusnadi et al., Functional Starch-Binding Domain of *Aspergillus* Glucoamylase I in *Escherichia coli*. Gene, 127(2):193-97, 1993.
Lawson et al., Nucleotide Sequence and X-ray Structure of Cyclodextrin Glycosyltranferase from *Bacillus circulans* Strain 251 in a Maltose-dependent Crystal Form. J. Mol. Biol. 236:590-600, 1994.
Ohdan et al., Introduction of Raw Starch-Binding Domains into *Bacillus subtilis* Alpha-Amylase by Fusion with the Starch-Binding Domain of *Bacillus* Cyclomaltodextrin Glucanotranseferase. Appl. Environ Microbiol., 66(7):3058-64, 2000.

(Continued)

*Primary Examiner*—Russell Kallis
(74) *Attorney, Agent, or Firm*—Amster, Rothstein & Ebenstein LLP

(57) ABSTRACT

The invention relates to a method for expressing a desired protein or polypeptide in a plant, in which the protein or polypeptide is expressed as a fusion with at least one starch binding domain. The plant is preferably a plant that contains or produces starch or starch granules in at least one of its parts, such as potato, sweet potato, cassava, pea, taro, sago, yam, banana and/or cereals such as rice, maize, wheat and barley. The protein or polypeptide can be an enzyme, in particular an enzyme that can convert, modify, alter, degrade or otherwise influence starch (granules); or can be a receptor or a structural protein. The invention further relates to the fusions thus obtained, to genetic constructs that encode the above fusions and to plants transformed with said constructs. The method of the invention can in particular be used to provide modified starches and/or to provide complexes of starch (granules) and the above fusions. In another embodiment, one or more starch binding domains are expressed in a plant, to provide a plant producing modified starches.

15 Claims, 4 Drawing Sheets

OTHER PUBLICATIONS

Ong et al., The Cellulose-Binding Domains of Cellulases: Tools for Biotechnology. Trends in Biotechnology, 7:239-43, 1989.

Penninga et al., The Raw Starch Binding Domain of Cyclodextrin Glycosyltranferase from *Bacillus circulans* Strain 251. J. Biol. Chem, 271(51):32777-32784, 1996.

Sorimachi et al., Solution Structure of the Granular Starch Binding Domain of Glucoamylase from *Aspergillus niger* by Nuclear Magnetic Resonance Spectroscopy. J. Mol. Biol., 259(5):970-87, 1996.

Sorimachi et al., Solution Structure of the Granular Starch Binding Domain of *Aspergillus niger* Glucoamylase Bound to Beta-Cyclodextrin. Structure, 5(5):647-61, 1997.

Svensson et al., Sequence homology between putative raw-starch binding domains from different starch-degrading enzymes. Biochem. J., 264:309-11, 1989.

* cited by examiner

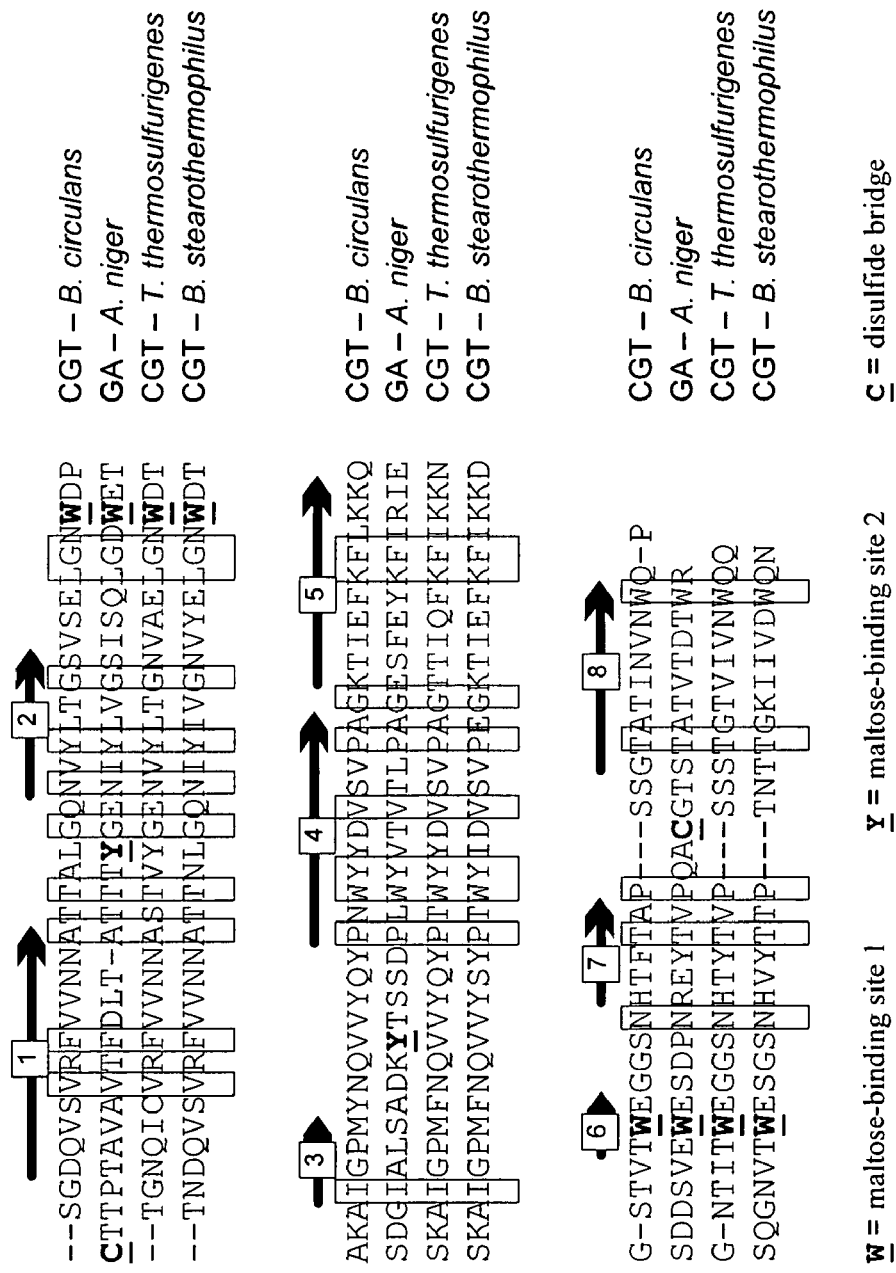
Figure 1: Alignment of starch-binding domains

Figure 2. Constructs for targeting proteins to starch granules
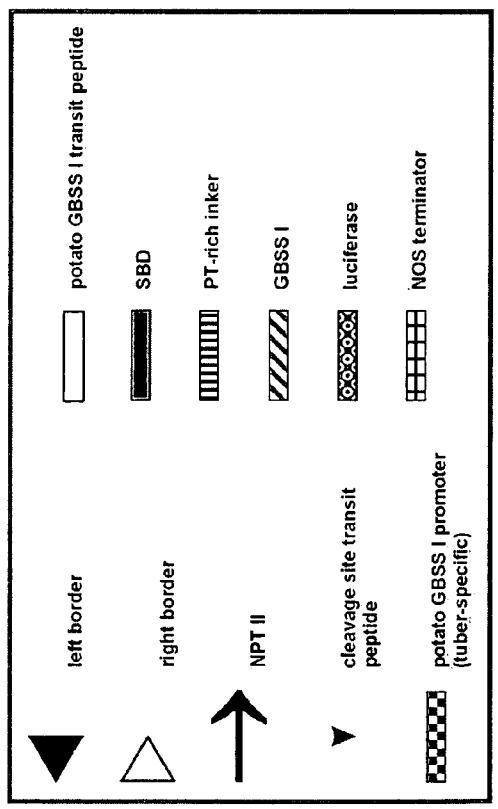
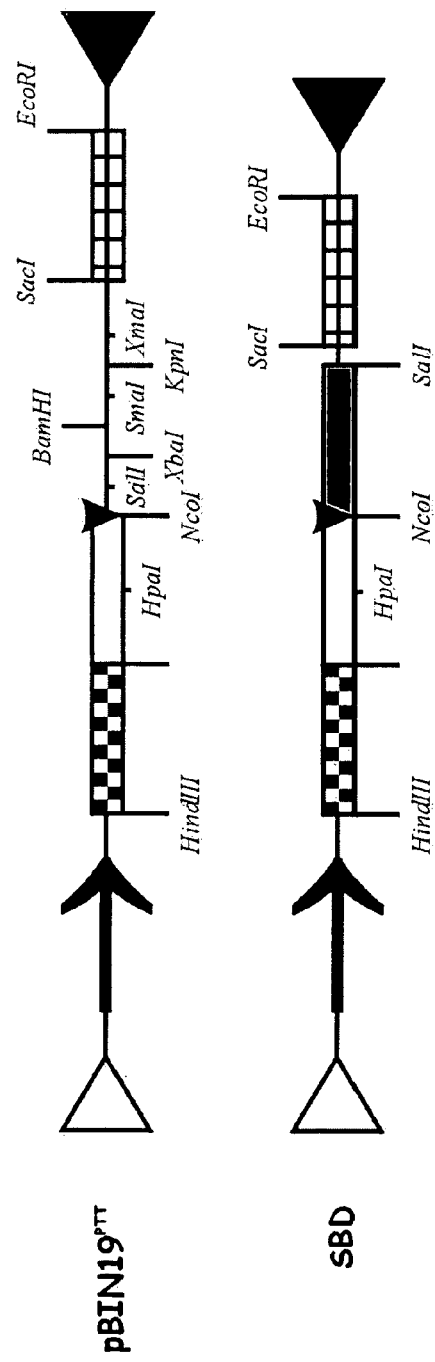

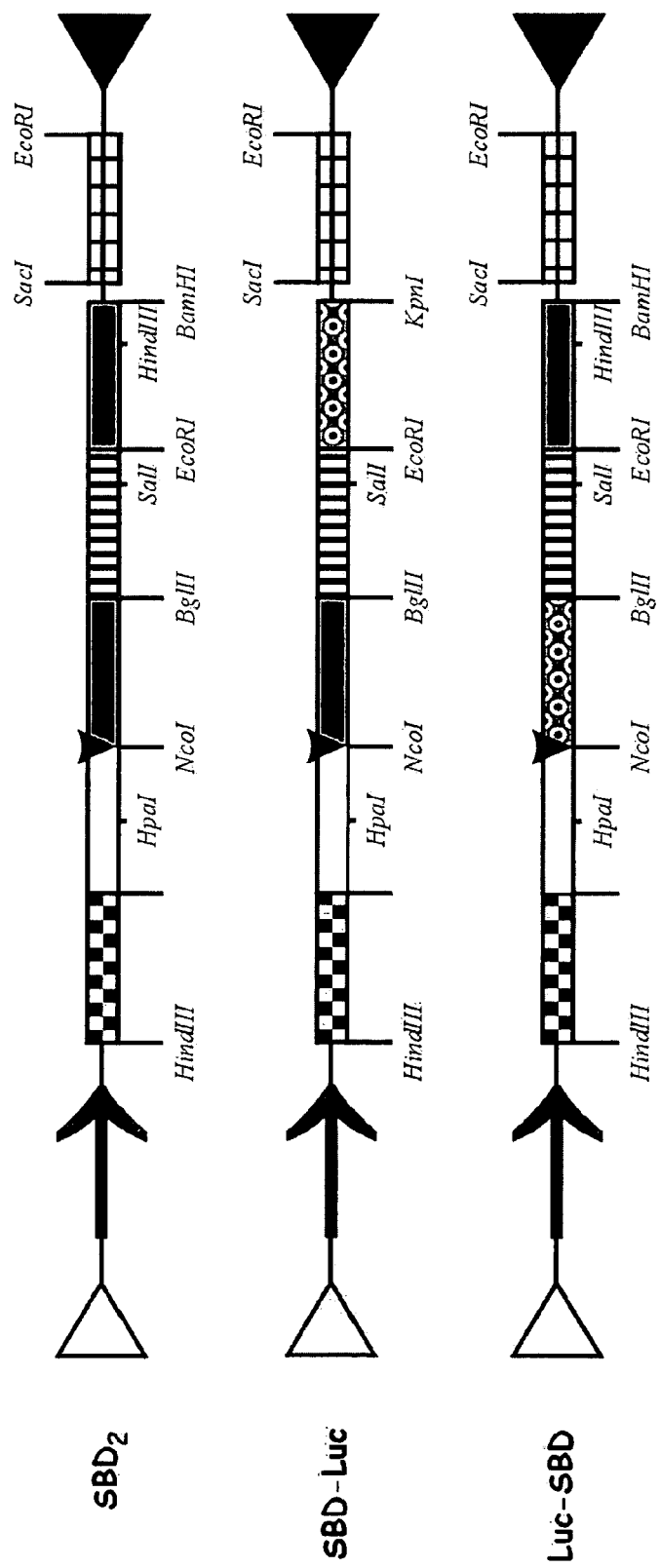
Fig. 2, contd.

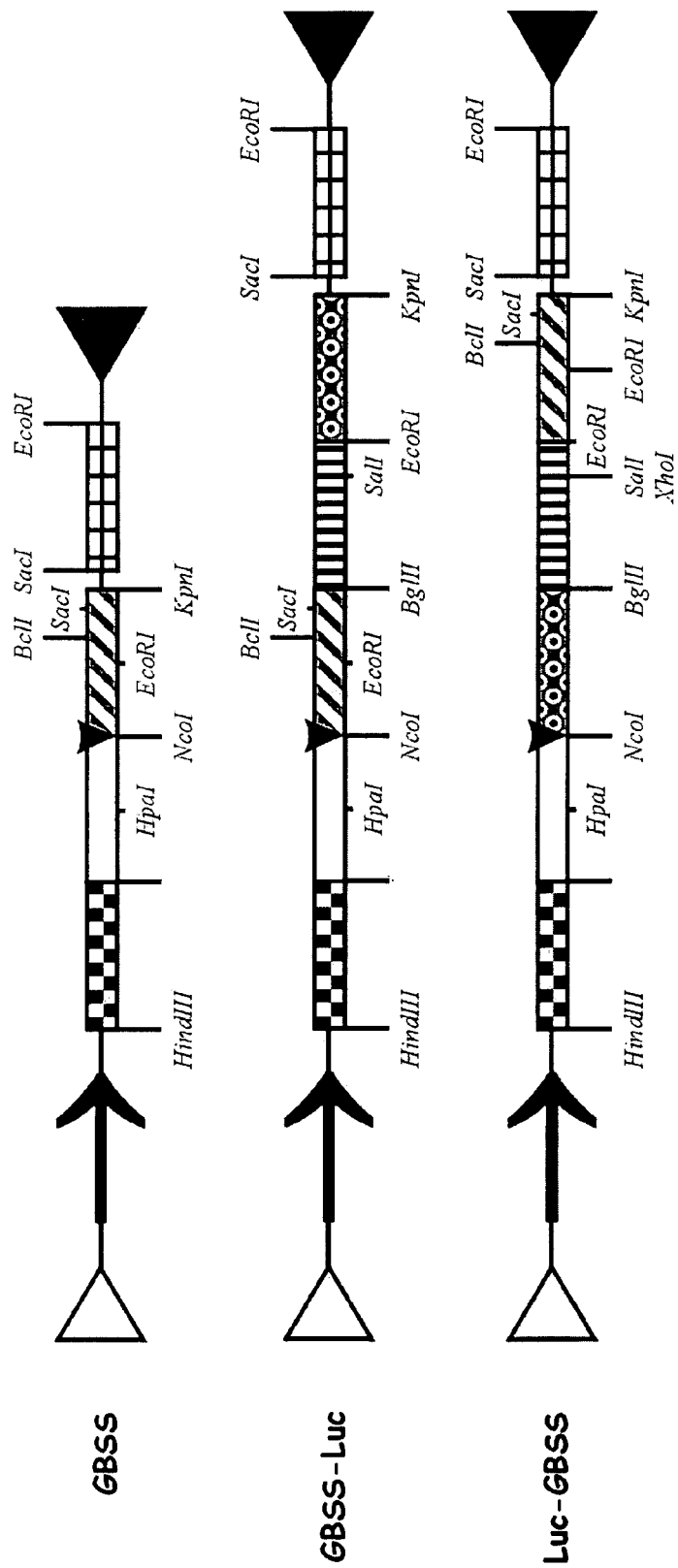
Fig. 2, contd.

SEQUENCE LISTING

<160> NUMBER OF SEQ ID NOS: 5

<210> SEQ ID NO 1
<211> LENGTH: 104
<212> TYPE: PRT
<213> ORGANISM: B. circulans

<400> SEQUENCE: 1

Ser Gly Asp Gln Val Ser Val Arg Phe Val Val Asn Asn Ala Thr Thr
1               5                   10                  15

Ala Leu Gly Gln Asn Val Tyr Leu Thr Gly Ser Val Ser Glu Leu Gly
            20                  25                  30

Asn Trp Asp Pro Ala Lys Ala Ile Gly Pro Met Tyr Asn Gln Val Val
        35                  40                  45

Tyr Gln Tyr Pro Asn Trp Tyr Tyr Asp Val Ser Val Pro Ala Gly Lys
    50                  55                  60

Thr Ile Glu Phe Lys Phe Leu Lys Lys Gln Gly Ser Thr Val Thr Trp
65                  70                  75                  80

Glu Gly Gly Ser Asn His Thr Phe Thr Ala Pro Ser Ser Gly Thr Ala
                85                  90                  95

Thr Ile Asn Val Asn Trp Gln Pro
            100

<210> SEQ ID NO 2
<211> LENGTH: 108
<212> TYPE: PRT
<213> ORGANISM: A. niger

<400> SEQUENCE: 2

Cys Thr Thr Pro Thr Ala Val Ala Val Thr Phe Asp Leu Thr Ala Thr
1               5                   10                  15

Thr Thr Tyr Gly Glu Asn Ile Tyr Leu Val Gly Ser Ile Ser Gln Leu
            20                  25                  30

Gly Asp Trp Glu Thr Ser Asp Gly Ile Ala Leu Ser Ala Asp Lys Tyr
        35                  40                  45

Thr Ser Ser Asp Pro Leu Trp Tyr Val Thr Val Thr Leu Pro Ala Gly
    50                  55                  60

Glu Ser Phe Glu Tyr Lys Phe Ile Arg Ile Glu Ser Asp Asp Ser Val
65                  70                  75                  80

Glu Trp Glu Ser Asp Pro Asn Arg Glu Tyr Thr Val Pro Gln Ala Cys
                85                  90                  95

Gly Thr Ser Thr Ala Thr Val Thr Asp Thr Trp Arg
            100                 105

<210> SEQ ID NO 3
<211> LENGTH: 104
<212> TYPE: PRT
<213> ORGANISM: T. thermosulfurigenes

<400> SEQUENCE: 3

Thr Gly Asn Gln Ile Cys Val Arg Phe Val Val Asn Asn Ala Ser Thr
1               5                   10                  15

Val Tyr Gly Glu Asn Val Tyr Leu Thr Gly Asn Val Ala Glu Leu Gly
            20                  25                  30

Asn Trp Asp Thr Ser Lys Ala Ile Gly Pro Met Phe Asn Gln Val Val
        35                  40                  45

-continued

```
Tyr Gln Tyr Pro Thr Trp Tyr Tyr Asp Val Ser Val Pro Ala Gly Thr
         50                  55                  60

Thr Ile Gln Phe Lys Phe Ile Lys Lys Asn Gly Asn Thr Ile Thr Trp
 65                  70                  75                  80

Glu Gly Gly Ser Asn His Thr Tyr Thr Val Pro Ser Ser Ser Thr Gly
                 85                  90                  95

Thr Val Ile Val Asn Trp Gln Gln
            100

<210> SEQ ID NO 4
<211> LENGTH: 105
<212> TYPE: PRT
<213> ORGANISM: B. stearothermophilus

<400> SEQUENCE: 4

Thr Asn Asp Gln Val Ser Val Arg Phe Val Val Asn Asn Ala Thr Thr
 1               5                  10                  15

Asn Leu Gly Gln Asn Ile Tyr Ile Val Gly Asn Val Tyr Glu Leu Gly
             20                  25                  30

Asn Trp Asp Thr Ser Lys Ala Ile Gly Pro Met Phe Asn Gln Val Val
             35                  40                  45

Tyr Ser Tyr Pro Thr Trp Tyr Ile Asp Val Ser Val Pro Glu Gly Lys
         50                  55                  60

Thr Ile Glu Phe Lys Phe Ile Lys Lys Asp Ser Gln Gly Asn Val Thr
 65                  70                  75                  80

Trp Glu Ser Gly Ser Asn His Val Tyr Thr Thr Pro Thr Asn Thr Thr
                 85                  90                  95

Gly Lys Ile Ile Val Asp Trp Gln Asn
            100                 105

<210> SEQ ID NO 5
<211> LENGTH: 24
<212> TYPE: PRT
<213> ORGANISM: Artificial Sequence
<220> FEATURE:
<223> OTHER INFORMATION: PT-rich linker peptide

<400> SEQUENCE: 5

Arg Ser Pro Thr Pro Thr Pro Thr Thr Pro Thr Pro Thr Pro Thr Thr
 1               5                  10                  15

Pro Thr Pro Thr Pro Ser Thr Glu
             20
```

EXPRESSION IN PLANTS OF STARCH BINDING DOMAINS AND/OR OF PROTEIN-FUSIONS CONTAINING STARCH BINDING DOMAINS

CROSS REFERENCE TO RELATED APPLICATIONS

This application is U.S. National Stage application of PCT/NL00/00406, filed Jun. 13, 2000, and also claims priority to European patent application 99201862.2, filed Jun. 11, 1999.

The present invention relates to methods for gene expression in plants.

In particular, the invention relates to the expression in plants of proteins and/or polypeptides—including enzymes—as fusions with improved affinity for starch, such as for the starch granules that may occur in plants in vivo, in particular in cellular organelles such as plastids More in particular, the invention relates to the expression in plants of proteins and/or polypeptides as a fusion with one or more moieties or domains that have affinity for starch, such as 'starch binding domains'.

Some further aspects of the invention reside in the protein fusions thus expressed, in gene constructs that encode such fusions, and in methods for the transformation of plants using such constructs as well as in the transformed plants thus obtained.

The invention can in particular be used for the expression in plants in vivo of enzymes as fusions that become associated with the starch granules that occur in (some of the cellular organelles of) such economically important plants as potato, sweet potato, cassava, pea, taro, sago, yam banana, and/or cereals such as maize, rice wheat, and barley. This may either facilitate the isolation of the enzymes thus expressed from the plant material, as well as their further use, and/or the enzymes thus expressed may be used to alter and/or otherwise influence the starch or starch granules leading to plants with improved properties, such as the production of modified starches. These and other applications of the invention will become clear from the description hereinbelow.

International application WO 98/14601 describes a hybrid polypeptide comprising: (a) a starch binding domain, and (b) a payload polypeptide fused to said starch binding domain. Said hybrid polypeptide may be expressed in any suitable host organism, such as in bacteria, plants and animals.

Said starch binding domain—referred to in WO 98/14601 as "starch-encapulating domain"—may be any starch-binding domain known per se, for instance derived from soluble starch synthase I, soluble starch synthase II, soluble starch synthase III, granule-bound starch synthase, branching enzyme I, branching enzyme IIa, branching enzyme IIBb or glycoamylase.

The general purpose of the method described in WO 98/14601 is to provide a "peptide-modified starch" (vide for instance page 10, line 20), i.e. the "encapsulation of desired amino acids or peptides within the starch and specifically within the starch granule" (page 6, line 28) to "increase the plants capacity to produce a specific protein, peptide or provide an improved amino acid balance." (page 21, line 1).

For instance, the method of WO 98/14601 may for instance be used "to make modified starches comprising the payload polypeptide" (page 7, line 8); "for providing polypeptide such as hormones or other medicaments, e.g. insulin, in a starch encapsulating form to resist degradation by stomach acids" (page 7, line 11); "for producing the payload polypeptides in easily purified form" (page 7, line 13); or "to enhance the amino acid content of particular amino acids in the modified starch" (page 8, line 1) to provide "grain feeds enriched in certain amino acids" (page 7, line 9).

As specific examples of payload polypeptides, WO 98/14601 mentiones "hormones, e.g., insulin, a growth factor, e.g. somatropin, an antibody, enzyme, immunoglobulin, or dye" (page 8, lines 7–9), as well as for instance prolactin, serum albumins and growth hormones (page 15, lines 1–16).

As preferred payload polypeptides, WO 98/14601 mentiones somatotropin, insulin A and B chains, calcitonin, beta endorphin, urogastrone, beta globin, myoglobin, human growth hormone, angiotensin, proline, proteases, beta-galactosidase, and cellulases (pages 15, lines 14–16).

However, none of these payload proteins or polypeptides is capable of "interacting" with starch or the starch granules as defined in this application.

More generally, WO 98/14601 does not describe fusions of at least one starch binding domain and at least one "starch-altering" enzyme as described hereinbelow, i.e. an enzyme that can convert, modify, alter, degrade or otherwise influence the starch, the starch granule or the structure or interactions thereof.

WO 98/14601 also does not describe, nor mentions as a purpose or as a possible application, the expression of fusions of at least one starch binding domain and an enzyme that can "interact with" starch and/or a starch granule in a plant, e.g. to provide a transgenic plant that is capable of producing a modified starches or modified starch granules as described hereinbelow, i.e. a starch (granule) that differs from the starch (granule) naturally provided by the plant in at least one property thereof, such as crystallinity, branching degree, glucan composition, oxidation, phosphorylation, etc.. (In this respect, it should be noted that where WO 98/14601 refers to a "modified starch", a "peptide-modified starch" is meant, e.g. "the naturally occuring starch (that) has been modified to comprise the payloadpolypeptide", vide page 9, lines 27–28. Compared to the corresponding native starch, such a "(peptide-)modified" starch according to WO 98/14601 will only be "modified" compared to the starch natively produced by the plant in that it comprises said protein or polypeptide.).

The international application WO 92/11376 describes a method for suppressing amylose formation in potato by transforming a potato plant with a construct comprising antisense fragments designed to inhibit (the expression of) the GBSS-gene. The Canadian patent application 2 061 143 describes a similar technique for producing amylose-free potato starch.

In starch-producing plants, starch is usually synthesized/ present in the form of starch granules. A number of enzymes in the plant are known to interact in vivo with these granules, for instance in order to build up, modify and/or degrade the starch molecules, the starch granules and/or the structure thereof. These include enzymes such as starch synthases, branching and debranching enzymes, etc., for which in general reference is made to A. M. Smith, K. Denyer and C. Martin, Annu. Rev. Plant Physiol. Mol. Biol.,1997, 48:67–87 and C. Martin and A. M. Smith, The Plant Cell, Vol. 7, 971–985, July 1995.

Such enzymes or mutants thereof may also be used to produce modified starches, either in vitro or in vivo. The production of modified starches by plants tranformed with (genes encoding) such enzymes is for instance described in DE-A-195 34 759, WO 92/14827 (in which a branching enzyme derived from potato cDNA is used) and WO 92/11376 (which describes an alternative method in which antisense DNA is used to suppress GBSS activity in plants.)

It is also known that some micro-organisms contain proteins/enzymes that can interact with (i.e. degrade, modify or convert) starch or starch granules, and some non-limiting examples thereof are mentioned below. Again, such enzymes and/or mutants thereof have been used in the art to produce modified starches in vitro and/or in vivo, the latter in plants transformed with (a) gene(s) encoding said enzyme or mutant. Reference is for instance made to WO 91/19808, U.S. Pat. No. 5,349,123 and U.S. Pat. No. 5,750,875, which describe plants transformed with bacterial amylases—and in particular cyclodextringlycosyltransferases (CGTases)—for the in vivo production of cyclodextrins.

Proteins/enzymes that can interact with starch, and in particular the enzymes from micro-organisms, generally contain—besides one or more catalytic domains—one or more regions that can bind to the starch and/or the starch granules. The latter are referred to in the art as "starch binding regions" or "starch binding domains". For a description of some starch binding domains that have been investigated in the art, reference is for instance made to Penninga et al., J. Biol. Chem, Vol. 271, No 51, 32777–32784, 1996, and Lawson et al., J. Mol. Biol. (1994) 236, 590–600, who describe the raw starch binding domain (E-domain) of CGTase from *B. circulans*; Sorimachi et al., J. Mol. Biol. (1996), 259, 970–987 and Structure 1997, Vol. 5, No.5, 647–661, who describe the starch binding domain of *A. niger* glucoamylase.

Svensson et al., Biochem. J. (1989), 264, 309–311, describe the sequence homology between putative starch binding domains from α-amylase from *Streptomyces limosus*, β-amylase from *Clostridium thermosulfurogenes*, glucoamylase from *A. niger*, maltogenic α-amylase from *Bacillus stearothermophilus*, maltotetraose-forming amylase from *Pseudomonas stutzeri*, CGTase from *Bacillus*, CGTase from *Klebsiella pneumoniae* and glucoamylase from *Rhizopus oryzae* (the latter being a N-terminal starch binding region). A similar comparison of different starch binding domains is also given by Janecek and Sivcek, FEBS letters 456 (1999), 119–125, published after the priority date of the present application.

It has also been suggested that some conserved tryptophan residues and the amino acids directly adjacent thereto may play an important role in starch binding, vide Goto et al., Appl. Environ. Microbiol., 1994, p. 3926–3930; Williamson et al., Biochemistry 1997, 36, 7535–7539, and Chen et al., Protein Engineering, vol. 8, 1049–1055 (1995).

WO 98/16190 describes fusion products of enzymes and one or more starch binding domains, as well as oral care compositions that contain such fusions. The fusions are prepared by expression of an appropriate expression vector in a suitable microorganism.

WO 99/15636 describes starch binding domains, and in particular the so-called "D-" and "E-domain" of the maltogenic amylase from *Bacillus stearothermophilus* C599, and expression thereof in a *Bacillus* host cell. WO 99/1536 also described fusions of said starch binding domain and a reporter gene such as gfp, in order to monitor the expression of the starch binding domains in the *Bacillus* host.

However, WO 99/15636 does not describe fusions of a starch binding domain and an enzyme that can interact with starch or a starch granule. Also, WO 99/15636 only describes expression in *Bacillus*.

Chen et al., in Gene 99, (1991), 121–126, and in Biotechnol. Prog. 1991, 7, 225–229, describe a fusion of β-galactosidase and the starch binding domain from an *Aspergillus* glucoamylase, plasmids encoding such a fusion, and expression of said fusion in *E. coli*. The starch binding region is used to increase the affinity of β-galactosidase for starch granules, in particular as an affinity tail for recovery or enzymatic immobilisation using native starch granules as an absorbent.

Dalmia et al., in Biotechnology and bioengeneering, Vol. 47, pp. 575–584 (1995), describe fusions of β-galactosidase and the starch binding domains of glucoamylase I of *Aspergillus awamori* and of cyclodextrin glucanotransferase (domain E of CGTase) from *Bacillus macerans*, respectively, plasmids encoding said fusions, and expression of said fusions in *E. coli*. The fusion proteins thus obtained are said to bind specifically to potato starch, corn starch, and cross-linked amylose. As a possible application, the use of the starch binding domains as an "affinity tag" is suggested. Similarly, Dalmia et al., in Enzyme Microb. Technol.,1994, vol. 16, describe fusions containing a starch binding domain from *A. niger* glucoamylase, which is again used as an affinity tail to facilitate the one-step purification of the target β-galactosidase.

The use of cellulose binding domains as an affinity tag for protein purification (i.e. a fusion of a cellulose binding domain from a cellulase and α-galactosidase) has also been described in the art, vide Ong et al., Trends in Biotechnology, 7, 239–243 (1989).

However, when the above references describe fusions of a starch binding domain and an enzyme, said fusions are expressed in a micro-organism such as *E. coli*. Also, the starch binding domain is included only as a "tail" or "tag" in order to facilitate the isolation and purification of the desired enzyme activity from the bacterial culture medium.

The expression and use of such fusions in plants in situ, in particular in association with starch granules and/or plastids, is not mentioned in the art. In particular, the expression in plants of fusions containing enzymes that can alter the properties of the starch (granules) present in the plant (for instance for the in vivo production of improved starches) has not been described or suggested.

It is general object of the invention to express desired proteins or polypeptides in plants in vivo in association with starch produced or present in the plant, in particular in association with the starch granules produced or present in a plant.

A further object of the invention is to provide a method for obtaining transformed plants that produce modified starches.

Other objects of the invention will become clear from the description and figures hereinbelow.

The above objects are achieved by expressing a desired protein or polypeptide that can interact with starch or starch granules, in the plant as a fusion with one or more starch binding domains.

By "interact with starch or starch granules" is generally meant that said protein or polypeptide can convert, modify, alter, degrade or otherwise influence the starch, the starch granule or the structure—and in particular the fine structure—or any interaction(s) thereof, and/or the physical and/or chemical properties of said starch (granule). Generally, this will result in a starch or starch granule that differs from the starch (granule) naturally provided by the plant in at least one property thereof (i.e. in addition to the presence of the fusion), such as crystallinity, branching degree, glucan composition, oxidation, phosphorylation, etc.

Usually, said protein or polypeptide will be an enzyme that can interact with starch or starch granules, including but not limited to the enzymes mentioned hereinbelow. Such enzymes will also be referred to as "starch altering enzymes", and the fusions of such starch altering enzymes with one or more starch binding domains will also be referred to as "starch altering fusion".

Thus, compared to the teaching of WO 98/14601, such a "starch altering fusion" according to the invention is capable of "actively" influencing at least one property of the starch (granule), e.g. as indicated below. For this purpose, the "starch altering enzyme" will be an enzyme that natively (i.e. also when not expressed as a fusion as described herein) shows some affinity and/or (enzymatic) activity towards starch (granules). In particular, these will be enzymes that as such already can convert, modify, alter, degrade or otherwise influence starch, a starch granule or the structure or any interaction(s) or properties thereof. In particular, these will be enzymes that as such can already alter at least one property of starch (granules), and in particular one or more of the properties 1–15 listed below.

By comparison, the proteins, polypeptides or enzymes that are mentioned for the fusions according to WO 98/14601 natively do not show any affinity and/or (enzymatic) activity towards starch (granules).

In its broadest sense, the invention relates to a method for expressing a desired protein or polypeptide in a plant, in which the protein or polypeptide is expressed as a fusion with at least one starch binding domain.

In particular, the invention relates to a method for expressing a desired protein or polypeptide in a plant, such that the desired protein or polypeptide becomes associated and/or can be obtained in association with any starch produced by or present in said plant, and in particular with any starch granules produced by or present in said plant or any part of said plant, in which the protein or polypeptide is expressed in vivo in the plant or any part thereof as a fusion with one or more starch binding domains.

More specifically, this method comprises the steps of:
a) providing a genetic construct comprising at least one nucleotide sequence encoding the desired protein or polypeptide combined with at least one nucleotide sequence encoding a starch binding domain;
b) transforming a plant with said genetic construct;
c) expressing said genetic construct in the plant in vivo.

Furthermore, as the starch granules in a plant will usually be present in cellular organelles within the plant cell, and in particular in plastids such as amyloplasts, chloroplasts and/or chromoplasts, the method of the invention can also be used to express a desired protein or polypeptide in association with such an organel.

In a further aspect, the invention relates to a fusion of at least one desired protein or polypeptide and at least one starch binding domain, as expressed in—or more generally as present in—in a plant or in any part of a plant, including the seeds, leaves, roots (including tuburous roots), tubers, stems, stalks, fruits, grains or flowers, and in particular the honey-producing parts of flowers, of a plant.

A further aspect of the invention relates to a genetic construct suitable for transforming a plant, comprising at least one nucleotide sequence encoding a desired protein or polypeptide combined with at least one nucleotide sequence encoding a starch binding domain.

Yet other aspects of the invention comprise a plant that has been transformed with a genetic construct as mentioned above, or a descendant thereof, and/or a plant that expresses a fusion as described above, preferably in conjunction with any starch (granules) present in or produced by said plant.

Further aspects of the invention will become clear from the description hereinbelow.

The protein or polypeptide that is expressed via the method of the invention can be any polypeptide or protein known per se, and is preferably an enzyme. The protein or polypeptide may or may not by itself have natural affinity for starch or starch granules. If the protein or polypeptide essentially does not have any affinity for starch (granules), or has only a very low affinity, the method of invention may be used to provide the protein or polypeptide with such affinity. If the protein or polypeptide has some natural affinity for starch (granules), such as enzymes that naturally interact with starch or starch granules, the method of invention may be used to increase said affinity, and/or to alter said affinity. For instance, it is known that starch may occur in different forms or states, which may for instance differ in crystallinity (i.e. amorphous vs crystalline) and/or in one or more other properties such as glucan content or degree of branching, and such different forms of starch may also form different parts or regions of one and the same starch granule. The method of the invention may therefore also be used to alter (such as increase or decrease) the affinity of enzymes for one or more such specific forms of starch, both in absolute terms as well as in relative terms (i.e. compared to the affinity for other forms of starch). In this way, the affinity of the enzyme for different starch granules and/or for different parts or regions of a single starch granule may also be altered (again both in absolute or in relative terms).

Therefore, a further aspect of the invention relates to a method for providing a protein or polypeptide with affinity for starch (granules), and/or for increasing the affinity of a protein or polypeptide for starch (granules), and/or for altering the affinity of a protein or polypeptide for starch (granules) comprising expressing the protein or polypeptide in a plant as a fusion with at least one starch binding domain.

More specifically, this aspect of the invention comprises the steps of:
a) combining a nucleotide sequence encoding the protein or polypeptide with at least one nucleotide sequence encoding a starch binding domain, so as to provide a genetic construct encoding a fusion of the protein or polypeptide and the at least one starch binding domain;
b) transforming a plant with said genetic construct;
c) expressing said genetic construct in the plant.

The (gene(s) encoding) the desired protein or polypeptide may be derived from any source, including from plants, animals, fungi, algae, yeasts, bacteria and/or other microorganisms, and may be homologous or heterologous to the plant in which the fusion is expressed.

Alternatively, (genes encoding) variants or mutants of such proteins or polypeptides may be used, such as those known per se in the art and/or obtainable via genetic manipulation techniques. These include mutant enzymes with altered properties compared to the enzyme from which they have been derived, such as altered substrate binding activity, altered substrate specificity, altered conversion properties and/or altered kinetic characteristics.

Furthermore, instead of the full protein or polypeptide as mentioned above, one or more fragments, parts, regions or domains thereof may be incorporated in and/or expressed as part of the fusions of the invention. Preferably, these fragments, parts, regions or domains are such that after expression, the fusion of the invention still provides the desired biological activity of the protein or polypeptide.

According to one preferred embodiment of the invention, the protein or polypeptide is an enzyme that can 'interact with' starch or starch granules, by which is meant that the enzyme can convert, modify, alter, degrade or otherwise influence the starch, the starch granule or the structure—and in particular the fine structure—and/or interactions thereof, and/or the physical and/or chemical properties of the starch (granule).

Some non-limiting examples of such ("starch altering") enzymes include, but are not limited to, different kinds of amylases (alpha-, beta, gluco-, iso-, etc.), CGTases, (neo) pullulanase, amylomaltase, glucan- and levansucrase, branching enzyme (such as glgB), fosforylating enzymes such as certain kinases, oxidative enzymes (such as oxidases and dehydrogenases), other starch-decorating enzymes (including those suitable for the transfer of sulfate and acetyl groups) and glycosyltransferases.

These enzymes may be obtained from any suitable source including bacteria, yeasts, fungi, algae and other microorganisms including but not limited to *Escherichia coli*, *Bacillus* (*subtilis*, *cereus*, *polymyxa*, *stearothermophilus*, *licheniformis*, *firmus/lentus*, *circulans*, *macerans*), *Aspergillus* (*niger*, *oryzae*, *kawachi*), *Klebsiella aerogenes*, *Streptomyces limosus*, *Pseudomonas* (*saccharophila*, *amyloderamosa*, *stutzeri*), *Clostridium* (*thermohydrosulfuricum*, *thermosulfurogenes*), *Microbacterium*, *Thermoanaero-bacterium thermosulfurigenes*, *Saccharomyces cerevisiae*, *Rhizopus oryzae*, *Streptococcus mutans*, *Leuconostoc mesenteroides*, *Neisseria polysaccharea* and/or *Aureobasidium pullulans*.

The enzymes may also be derived from higher forms of life including plants and animals. Some examples of plant-derived enzymes include starch synthases, starch-branching and -debranching enzymes (including isoforms thereof, such as BE-I and BE-II), disproportionating enzymes, putative potato kinase (sometimes also referred to as R1) etc., as well as the further enzymes mentioned in A. M. Smith et al. and C. Martin and A. M. Smith, above.

Other suitable starch-altering enzymes are for instance described in U.S. Pat. No. 5,665,585.

In particular, the expression in a plant of a fusion of at least one starch binding domain and an enzyme that can interact with starch or starch granules as defined hereinabove will lead to (a transformed plant that produces) a starch (granule) of which at least one property has been altered, compared to the starch (granule) natively produced by said plant (in which the presence of the fusion as such is not taken into account).

More in particular, such expression of a "starch altering fusion" will lead to (a transformed plant that produces) a starch (granule) of which at least one of the properties 1–15 listed hereinbelow has been altered, compared to the starch (granule) natively produced by said plant (in which these properties and any alterations therein compared to the "wild type" starch can be determined in any manner known per se, including but not limited to the methods indicated below):

1. Morphology (microscopy [Kuipers et al. (1994) Plant Cell 6, 43–52; Edwards et al. (1999) Plant J. 17, 251–261])
2. Granule size distribution (Coulter multisizer [analysis follows the instructions of the manufacturer])
3. Amylose:amylopectin ratio (many different methods including iodine-staining combined with optical density measurements [Hovenkamp-Hermelink et al. (1988) Potato Res. 31, 241–246], size-exclusion CL2B chromatography [Denyer et al. (1995) Plant Cell Environment 18, 1019–1026])
4. Molecular weight of the constituent polymers (size-exclusion CL2B chromatography [Denyer et al. (1995) Plant Cell Environment 18, 1019–1026])
5. Degree of branching (among others: debranching of gelatinized starch followed determination the chain length distribution of the forth-coming digest by high-performance size-exclusion chromatography [Kossmann et al. (1999) Planta 208, 503–511], high-performance anion-exchange chromatography [Safford et al. (1998) Carbohydrate Polymers 35, 155–168; Kossmann et al. (1999) Planta 208, 503–511], or MALDI-TOF mass spectrometry)
6. Different distribution of glycosidic linkages (enzymic digestion of starch with isoamylase, alpha- or beta-amylase [Colonna and Mercier (1984) Carbohydrate Research 126, 233–247; Safford et al. (1998) Carbohydrate Polymers 35, 155–168; Kossmann et al. (1999) Planta 208, 503–511], followed by chromatography to purify the obtained fragments [Safford et al. (1998) Carbohydrate Polymers 35, 155–168], and subsequent analysis by mass spectrometry and or NMR [Fontaine et al. (1993) Journal Biological Chemistry 268, 16223–16230])
7. Different decoration patterns with substituents, such as phosphate groups (several methods, including NMR [Blennow et al. (1998) Carbohydrate Research 307, 45–54; Safford et al. (1998) Carbohydrate Polymers 35, 155–168] and glucose-6-phosphate/total phosphate determination [Visser et al. (1997) Starch 49, 443–448])
8. Crystallinity (X-ray diffraction [Buleon et al. (1998) Macromolecules 31, 6605–6610; Bogracheva et al. (1999) Carbohydrate Polymers 39, 303–314])
9. Degree of cross-linking (X-ray diffraction [Buleon et al. (1998) Macromolecules 31, 6605–6610; Bogracheva et al. (1999) Carbohydrate Polymers 39, 303–314], differential scanning calorimetry [Visser et al. (1997) Starch 49, 443–448])
10. Gelatinization (differential scanning calorimetry [Visser et al. (1997) Starch 49, 443–448], Bohlin viscosimetry [Visser et al. (1997) Starch 49, 443–448])
11. Retrogradation (Bohlin viscosimetry [Visser et al. (1997) Starch 49, 443–448])
12. Solution properties such as viscosifying potential (Bohlin viscosimetry [Visser et al. (1997) Starch 49, 443–448])
13. Water-binding or swelling potential of the granules [Visser et al. (1997) Starch 49, 443–448]
14. Gel strength, adhesiveness, cohesiveness, elasticity and hardness (texturometer [Visser et al. (1997) Starch 49, 443–448]); and/or
15. Film-forming properties.

Preferably, the above properties, when mentioned via the method indicated, will be altered by at least 1%, preferably at least 5%, more preferably at least 10%, compared to the corresponding "wild type" starch (granule).

Some non-limiting examples of other proteins or polypeptides (i.e. non-enzymatic) that may be expressed in association with starch (granules) according to the invention include proteins or polypeptides derived from micro-organisms, plants or animals, such as receptors (such as estrogen receptors and in particular plant hormone receptors) and other structural proteins, such as protein "zippers".

According to one embodiment of the invention, the desired protein or polypeptide is not β-galactosidase or another reporter enzyme.

The term 'starch binding domain' or 'SBD' is well-known in the art, for instance from the references cited hereinabove, and is generally used to denote any part, region or domain of a protein or polypeptide, and in particular of an enzyme, that has natural affinity to (i.e. that binds to, attaches to, complexes with or otherwise associates with) starch or starch granules, or more generally with polymers of glucans.

Any naturally occuring starch binding domain, or any part or fragment thereof that still has affinity for starch (granules), may be used, as well as variants or mutants thereof.

As such, the starch binding domain(s) used in the invention may be derived from any protein or polypeptide known per se that contains one or more starch binding domains, including proteins or polypeptides derived from plants, animals, fungi, algae, yeasts, bacteria and/or other microorganisms. The starch binding domains may be homologous or heterologous to the plant in which the fusion is expressed. Preferably, a starch binding domain of an enzyme is used, more preferably an enzyme derived from a bacterium, yeast, fungus or (other) micro-organism, or of a plant, such as GBSSI, which occurs in many different plants.

Some non-limiting examples of enzymes from which the starch binding domains may be derived are mentioned in the prior art indicated above, and may further include enzymes from bacteria, yeasts, fungi, or other micro-organisms such as the cyclodextrin glycosyl transferases ("CGTases"), for instance from *Bacillus circulans, Aspergillus awamori, Aspergillus kawachi, Klebsiella pneumoniae* or *Bacillus staerothermophilus*; SBDs derived from thermostable enzymes, such as the CGTase of *Thermoanaerobacterium thermosulfurigenes*; glucoamylases, for instance from *Aspergillus niger* (which is reinforced by a disulfide bridge); glucoamylase from *Rhizopus oryzae*, alpha-amylase from *Streptomyces limosus*, beta-amylase from *Clostridium thermosulfurogenes*, maltogenic alpha-amylase from *Bacillus stearothermophilus*, maltotetraose-forming amylase from *Pseudomonas stutzeri*; as well as enzymes from plants or animals such as granule-bound starch synthase I (GBSSI), partially granule-bound SSI, SSII and SSIII, a putative kinase (R1), and other granule-associated enzymes, as well as engineered forms of such domains.

Other suitable starch binding domains include for instance those derived from the enzymes mentioned in U.S. Pat. No. 5,665,585, as well as the natural starch binding domains and variants thereof described by Penninga et al., Lawson et al., Sorimachi et al., Svensson et al., Goto et al., Williamson et al., Chen et al. and Dalmia et al, above.

Although generally, all starch binding domains known per se can be used in the invention, including but not limited to those indicated above, it should be understood that for some applications of the invention, some starch binding domains may be preferred compared to others.

For instance, for the modification of the properties of (a) starch (granule), it may be that some types of starch binding domain (e.g. SBD) may direct the starch altering enzymatical activity fused with said starch binding domain towards the surface of the starch granule—for instance so as to alter one or more of the properties of and/or associated with said surface—whereas other types of starch binding domains may cause the starch altering enzymatical activity fused with said starch binding domain to be incorporated/enclosed within the starch granule.

In this way, the invention may not only make it possible to use a starch altering fusion as described herein to alter the properties of the starch (granule), but also to determine to at least some extend where said starch altering fusion effects its starch altering activity, e.g. within the starch granule and/or at the surface of the starch granule. In this respect, for a desired alteration of a property of the starch (granule), the skilled person will be able to select, based upon the teaching provided herein, both a suitable starch altering enzymatical activity as well as a suitable starch binding domain, which allows said enzymatical activity to be effected as efficiently as possible and/or at the desired site (e.g. the surface of the starch and/or within the starch granule).

Also, it is to be understood that although it is preferred in the invention to use only those parts or regions of the abovementioned enzymes, proteins or polypeptides that form the "starch binding domain(s)", it is not excluded that one or more other parts or sequences of the original enzyme may also remain or be present in the fusions of the invention (i.e. attached to the starch binding domain). It may even be possible to use the full amino acid sequence of the original enzyme as a starch binding domain in the invention, i.e. as a fusion with the desired enzyme, protein or polypeptide. When such further parts or sequences are (still) present, these most preferably (no longer) show any biological activity per se. When a full sequence is used as a starch binding domain, this sequence has preferably been made devoid of biological activity (e.g. made catalytically inactive), although again the invention in its widest sense is not limited thereto.

Some preferred examples of enzymes that can be used as starch binding domains in the invention (i.e after they have been made catalytically inactive) include catalytically inactive GBSS I or gbSSII.

Generally, such starch binding domains are polypeptides of about 95 to about 105 amino acids amino acids, although their size is not essential in the invention. For instance, when catalytically active enzymes such as GBSSI or gbSSII or parts thereof are used, they may have a size of about 525–770 amino acids. For some specific applications, such large starch binding groups may be preferred, but generally smaller size SBD's (i.e. up to about 150 a.a.) will be preferred.

According to one embodiment, the starch binding domain used in the invention contains at least one of the minimal sequences shown in FIG. 1, or a variant or mutant thereof, for instance in which one of the tyrosine residues in binding site 2 have been replaced by tryptophan.

Other suitable starch binding domains can be identified by means of sequence alignment of the above minimal sequences of FIG. 1 with a known database, for instance an alignment program known per se such as BLAST or PC gene. In general, any domain or region of an enzyme that contains a sequence that has a sequence homology of more than 50%, preferably more than 70%, more preferably more than 90% with the abovementioned minimal sequence as can be used (in which a deletion or insertion is counted as a single mutation).

Preferably, any binding domain used in the invention has an affinity for starch (granules) (expressed as $K_{ad}$-value) of more than 10, preferably more than 15 ml/g, as measured by means of adsorption isotherm methodology as described by Chen et al, for instance in the Protein Engineering-, Biotechnol. Prog.- and/or Gene-references mentioned above. In general, this involves measuring the absorption of the binding domain to native starch at different concentrations of the protein (i.e. of the binding domain). After mixing the protein (for instance in concentrations ranging from 0,1 to 1,0 mg/ml) and the starch (for instance 0,1 g) in a suitable aqueous medium (for instance 1 ml total volume), the mixture is shaken for a suitable period of time (for instance 20 min to 1 hr) at a suitable temperature (for instance 4° C.), after which the mixture is subjected to centrifugation (for instance 17400 g for 20 min), after which the protein concentration of the supernatant is assayed and the amount of adsorbed protein is determined by subtraction. Values for the absorption constant ($K_{ad}$) can then be derived from the slopes of the linear adsorption isotherms, optionally by comparison with a reference protein.

Also, preferably, the entire fusion of the invention also has an affinity for starch (again expressed in terms of $K_{ad}$-value) of more than 10, preferably more than 15 mL/g.

With respect to the affinity for starch and the $K_{ad}$-value, it will further be clear to the skilled person that these may also be influenced by factors usch as the type of starch used, the presence of glycosylation, the size of the fusion, the type of linker (if any) etc. Also, other assays for determining the affinity of a protein to starch have been described in the art, and these can also be used to identify suitable domains or regions.

In another embodiment of the invention, and as an alternative for starch binding domains, domains or regions with affinity for other glucan polymers such as cellulose, amylose, or amylopectin, glycogen, mutan, dextran, nigeran, pullulan, or affinity for fructan, pectin, xylan, or (mixed linkage) betaglucan polymers may be used. These include for instance enzymes or proteins for glucan polymers other than starch such as the glucan binding domains of sucrases, cellulose binding domains (which however have no or very low affinity for starch, and are therefore less preferred), granule-bound starch synthase I or part thereof, as well as engineered sucrose porin, maltose binding protein, maltoporin and/or lamB from *E. coli*, which have affinity for maltose/maltodextrin (The latter, however, have the disadvantage of a large size, i.e. about 400–600 amino acids, and also have little or no affinity for so-called raw starch).

Such cellulose binding domains, maltose binding proteins etc. can be used/expressed in a fusion of the invention analogously as described herein for the starch binding domains, to provide fusions with affinity for, and/or that can associate with, cellulose and maltose/maltodextrin, respectively. However, the use of starch binding domains, so that the resulting fusion can associate with starch (granules), is much preferred.

In the fusions expressed according to the invention, the desired protein or polypeptide may be fused directly with the one or more starch binding domains, or via a linker sequence, i.e. a sequence of 1–100, preferably 4–60 (optionally glycosylated) amino acids that connects the protein or polypeptide with the one or more starch binding domains. The linker sequence may also act as a "hinge" and/or spacer, for instance in order to ensure that the presence of the starch binding domain or the binding thereof to the starch (granule) does not interfere with or detract from the desired activity or properties of the enzyme, protein or polypeptide (and visa versa).

In principle, any natural or synthetic amino acid sequence can be used as a linker, preferably a sequence that essentially does not interfere with either the affinity of the starch binding domain for the starch (granules), or with the desired activity of the enzyme.

Some non-limiting examples of suitable linker sequences include:
the 40 AA linker sequence used in *Trichoderma*, comprising a flexible part and glycosylated rigid part;
naturally occurring or synthetic sequences of alternating Pro-Thr;
linker sequences containing major amount glycine residues or of (optionally O-glycosylated) serine or threonine residues.

Other suitabe linkers are for instance described by P. Argos, J. Mol. Biol. (1990), 211, p. 943–958.

The protein or polypeptide may also be bound to the one or more starch binding domains via an amino acid sequence that can be cleaved, i.e. chemically or preferably enzymatically. Examples are amino acid sequences that provide enzymatic cleavage site for enzymes such as thrombin, factor Xa, and collagenase can be mentioned. Such a sequence may also form part of a larger linker sequence as described above.

In the fusions of the invention, the one or more starch binding domains may be at the N'-terminus of the fusion, at the C' terminus of the fusion, or—if two or more starch binding domain are present—both. If a starch binding domain is used that is naturally (i.e. in the enzyme from which it has been derived) is at the C' terminus (or N' terminus), it is preferably also at the C' terminus (or N' terminus, respectively) of the fusion of the invention, although the invention is not limited thereto.

Also, when a fusion to the invention contains two or more starch binding domains, these may be the same or different (such as different domains from the same enzyme or domains from different enzymes/sources) and may—if present at the same terminus—also be fused directly or via a linker sequence, that again may also act as a hinge and/or spacer.

Furthermore, although usually not preferred, it is also possible that a fusion of the invention (a "bifunctional fusion") contains two or more of desired enzymes, proteins or polypeptides, which may be fused directly, via a linker sequence, or via a sequence encoding one or more starch binding domains (besides any further starch binding domains that may be present at the 3' and/or 5' end). For instance, there are cellulases and xylanases with "internal" cellulase binding domains, which may be included "internally" between two catalytic centers of the bifunctional fusion.

The fusions of the invention are obtained by expression in a plant in vivo of a nucleotide sequence (genetic construct) that codes for the fusion of the invention. For this purpose, the plant may be or may have been transformed with said genetic construct, or may be a descendant (such as obtained via sexual or asexual multiplication, including crossing and/or other breeding techniques) of a plant that has been transformed with such a genetic construct, and that has inherited the genetic construct.

The plant may be any monocotylous or dicotylous plant in which the fusions can be expressed, but is preferably a plant that naturally contains or produces starch, and more preferably a plant that contains or produces starch granules, either throughout the entire plant or in any part thereof, including seeds, leaves, roots (including tuburous roots), tubers, stems, stalks, fruits, grains or flowers, and in particular the honey-producing parts of flowers; and such a plant is referred to herein as a 'starch granule producing plant'. As mentioned above, said starch granules will usually be associated with or present in specific organelles of the plant cell, and in particular the plastids, such as chloroplasts, amyloplasts and/or chromoplasts.

Some preferred non-limiting examples of starch granule producing plants suitable for use in the invention include economically important crops such as potato, sweet potato, cassava, pea, taro, sago, yam, and/or cereals such as rice, maize, wheat and barley; of which potato, sweet potato, maize and wheat are especially preferred.

The starch granule producing plant may also be a plant, and in particular a genetically modified plant, that as such already produces a modified starch, such as transformed potato plants producing mutant amylose free ("amf") starch. For some applications, the use of a plant that produces starch granules that contain pores may be useful, in particular when the further use of the starch granules associated with the fusions of the invention involved diffusion of compounds in and out of the granules. For instance, some cereal starches are known to have natural pores. Also, the use of small granules, again as for instance in cereal starches, may also be advantageous with respect to diffusion of substances into the starch granule. Alternatively, a (pre)treatment with an enzyme that make pores or holes in starch granules, such as those of microbial origin, may be used.

A genetic construct encoding a fusion of the invention may be obtained by 'combining' the nucleotide sequence(s) encoding the at least one desired protein or polypeptide with at least one nucleotide sequence that codes for a starch binding domain, optionally with or via one or more sequences that encode a linker sequence as described above, in such a way that expression of the combined sequences in the desired plant leads to the formation of the fusion.

Generally, this involves covalently binding the nucleotide sequences in the same reading frame and in the same orientation, and in the correct order from the 5' end to the 3' end. This can be carried out using genetic manipulation techniques known per se, such as those described in Sambrook et al, "Molecular Cloning: A Laboratory Manual" (2nd.ed.), Vols. 1–3, Cold Spring Harbor Laboratory (1989); or F. Ausubel et al, eds., "Current protocols in molecular biology", Green Publishing and Wiley Interscience, New York (1987)

The one or more sequence(s) encoding the starch binding domains can be provided synthetically using known DNA synthesis techniques, but are preferably isolated from the organism from which the starch binding domain has been derived (i.e. in which it naturally occurs). Similarly, the sequence encoding the protein or polypeptide is also preferably isolated from a suitable biological source, and as such may be a nucleotide sequence encoding the mature protein, or a nucleotide sequence encoding a precursor thereof, that can be converted into the mature protein or polypeptide by post-translational modification(s) in the plant (i.e. as part of the encoded fusion).

The genetic construct encoding the fusions of the invention may further contain all other elements known per se for nucleic acid sequences or genetic constructs, such as promoters or other control elements, terminators, translation or transcription enhancers, integration factors, signal sequences, selection markers, etc., that are preferably suited for use in (the transformation of) the host plant. The sequences that encode these further elements of the construct may again be either isolated from a suitable biological source, or provided synthetically. Examples of suitable elements are for instance described in DE-A-195 34 759, WO 91/19808, U.S. Pat. No. 5,349,123, U.S. Pat. No. 5,750,875 and WO 92/14827.

The one or more nucleotide sequences encoding the further elements of the construct can again be combined with the nucleotide sequence encoding the fusion in a manner known per se, such as described in Sambrook et al., Ausubel et al., DE-A-195 34 759, WO 91/19808, U.S. Pat. No. 5,349,123 or U.S. Pat. No. 5,750,875.

Preferably, they are combined in such a way that—after transformation—the construct can be used for the expression of the fusion in the desired plant. Generally, this involves combining the control elements and any further elements with the sequence encoding the fusion in an operable manner, i.e. in the same reading frame and in the same orientation, and in the correct order from the 5' end to the 3' end.

The promoter can be any promoter that is able to control/induce the expression of the fusion in the intended plant, including constitutive and inducable promoters, and may be homologous or heterologous to said plant.

Also, a promoter may be used that directs the expression of the fusion to a specific part or tissue of the plant, and in particular to a tissue or part of the plant where starch (granules) are formed or present, including the including seeds, leaves, roots (including tuburous roots), tubers, stems, stalks, fruits, grains or flowers, and in particular the honey-producing parts of flowers, etc. Furthermore, a promotor may be used that induces expression of the fusion during a specific period in the life cycle of the plant. For instance, in potato, a promotor may be used that specifically directs the expression of the fusion in or to the tuber, and/or that allows for expression only during the time the plant forms its tubers.

Examples of suitable promoters include the CaMV promotor, GBSS promotor, patatin promotor, Ubiquitin promotor, ST1 promotor, TR1 promotor, napin promotor, as well as for instance the promoters described in DE-A-195 34 759, WO 91/19808, U.S. Pat. No. 5,349,123, U.S. Pat. No. 5,750,875 and WO 92/14827. For specific expression of foreign genes in potato tubers, reference is made to for instance EP 0 375 092 and Rocha-Sosa et al., EMBO J. 8, 23–29 (1989).

The construct of the invention may also comprise one or more sequences that encode signal proteins, including pre-, pro- of prepro-sequences. These usually precede the sequence encoding the fusion, such that the fusion is expressed as a (further) fusion with these signal proteins. The signal sequence may ensure any post-translational modifications required for the formation of the mature fusion (i.e. of the protein/polypeptide and/or the starch binding domain(s) part thereof), and/or may specifically direct the expressed fusion to a desired part or organel within the plant or plant cell, and in particular to the starch granule(s). In particular, signal sequences for plastide targeting, such as for amyloplast, chloroplast or chromoplast targeting can be used, or signal sequences for targeting the vacuole. Some non-limiting examples thereof include the small subunit RuBisCo, GBSS transit peptides and sporamine transit peptide.

According to one preferred embodiment, the genetic construct encoding the fusion is preferably in a form suitable for transformation of a plant, such as a vector or plasmid. As such, the construct is preferably such that upon transformation it is incorporated into the (genomic) DNA of the plant. However, the construct may also be in any other form that can provide for expression of the fusion in the plant, and that preferably also can be stably and/or independantly maintained and/or replicated in the plant, and/or inherited from one generation of the plant to the next. The construct is preferably further in a form that can be stably and/or independantly maintained and/or replicated in any organism to be used for constructing or selecting the construct and/or to be used in transforming the plant, such as *Agrobacterium*.

A further aspect of the invention therefore relates to a bacterium, virus or other organism suitable for transforming a plant, containing a genetic construct as defined above, and preferably capable of transferring said construct into a plant. The organism may for instance be a strain of *Agrobacterium*.

After construction, the construct is transformed into the desired plant, preferably a starch granule producing plant as defined above. Any technique for the transformation of a plant known per se can be used. Examples thereof include transformation using *A. tumefaciens* or *A. rhizogenes*, electroporation of tissues and/or protoplasts, particle bombardment, use of virusses for DNA delivery, etc., as well as the techniques described in DE-A-195 34 759, WO 91/19808, U.S. Pat. No. 5,349,123, U.S. Pat. No. 5,750,875 and WO 92/14827

After transformation, a plant is (re)generated from the transformed cells or tissue and the construct is expressed in the plant or part thereof, optionally upon induction thereof in a suitable manner.

The invention therefore also relates to a method for providing a plant that expresses a fusion as described above, comprising at least one step of:

a) transforming a plant with a genetic construct as described above, such that said genetic construct is expressed in the plant or at least part thereof, and optionally further comprising at least one step of:

b) providing descendants and/or further generations of the thus transformed plant, for instance via sexual or asexual multiplication, including crossing and/or other breeding techniques.

The invention also relates to seeds, tubers, seedlings, stakes (e.g. for cassava) or other cultivating material of such a transformed plant.

Upon expression, the fusion will usually become 'associated with' any starch granules present in the plant, by which is meant that the fusion attaches to, binds to, complexes with or otherwise combines with the starch granule, i.e. via the one or more starch binding domains present in the fusion. Said association may be such that the fusion is present on the surface of the starch granule, and/or incorporated into (such as by encapsulation or enclosure) the starch granule (e.g. during the biosynthesis thereof). The association(s) thus obtained will be collectively referred to hereinbelow as the 'complex'. One preferred embodiment of the invention concerns these complexes, methods for their preparation by expression in a plant, and plants that express these complexes.

As mentioned above, the starch granules in a plant will usually be present in or associated with specific organelles within the plant cell, and in particular the plastids, such as the amyloplasts, chloroplasts or chromoplasts. It should be understood that when in the present description and claims mentioned is made of a "starch granule", this is also meant to include (the starch granules as present in) these organelles. The term "complex" as mentioned herein therefore also includes complexes of fusions of the invention and such organelles.

Therefore, in another aspect, the invention relates to a method for producing a complex of at least one protein or polypeptide and a starch granule, comprising at least one step of:

a) expressing the protein or polypeptide as a fusion with at least one starch binding domain, in a plant that contains or forms starch granules;

and optionally comprising at least one further step of:

b) isolating the protein or polypeptide from the plant or any part thereof as a complex of the fusion and the starch granule.

A further aspect of the invention relates to a complex, comprising a fusion of a protein or polypeptide and at least one starch binding domain, associated with a starch granule.

In particular, this aspect of the invention relates to such a complex as expressed in/obtained from a plant via the method described above.

Yet another aspect of the invention therefore relates to a method for providing a plant that can produce a complex of a fusion as described above and a starch granule, comprising at least one step of:

a) transforming a starch granule producing plant with a genetic construct as described above, such that said genetic construct is expressed in the plant or at least part thereof;

and optionally further comprising at least one step of:

b) providing descendants and/or further generations of the thus transformed plant, for instance via sexual or asexual multiplication, including crossing and/or other breeding techniques.

The invention further relates to the complex-producing transformed plants thus obtained, or any descendant thereof, as well as cultivation material of said plant, including seed, tubers, stakes or seedlings.

Usually, and preferably, the fusion and the starch granule will already associate in vivo, so that they can be obtained/isolated together, using techniques known per se for the isolation of the starch granules from the plant or plant material. However, the invention is not limited thereto. For instance, the complex may also be formed during or as a result of the isolation/further processing of the plant or plant material, for instance when the fusion is expressed in a part of the plant (cell) separate(d) from the starch granule. In yet another embodiment, starch granules, optionally combined with a further carrier or matrix, can be used to selectively isolate the fusion from the plant (material), i.e. by a method comparable to an affinity technique.

Again, instead of isolating the starch granules, it may be easier and/or advantageous to isolate the organelles in which the starch granules are present, again in a manner known per se, so as to provide complexes of the starch granule containing organel and the fusion of the invention. These may also be used as such in any subsequent application(s).

The above aspect of the invention is particularly suited for producing a desired protein or polypeptide in for instance potato tuber, cassave root, sweet potato tuber, grains of maize, wheat and barley, as well as in peas, etc. After the tubers, roots or grains produced by the plants expressing the fusions have been harvested, the protein or polypeptide can be conveniently isolated therefrom as a complex with the starch granules. This aspect thus provides for a very efficient production and isolation of any desired protein or polypeptide, and may be used to produce such a polypeptide or protein in major and/or commercial amounts.

The complex thus obtained may be processed further, for instance for further purification, in which the fact that (essentially only) the desired protein or polypeptide is present as a complex with the starch granules may be used with advantage. The fusion may also be separated from the starch granules, and/or the fusion may be cleaved (i.e. at a suitably situated enzymatic cleavage site as described above) in order to provide the desired protein or polypeptide.

Compared to the expression of fusions in bacterial expression hosts such the E. coli strains described in the art, expression of the desired proteins or polypeptides according to the invention in (edible) plant material such as potato tubers may be advantageous from a safety standpoint. Also, expression of the desired protein or polypeptide in a plant host compared to a bacterial host may be advantageous for some applications, for instance when a bacterial host does not carry out all desired post-translational modifications or conversly degrades or otherwise detracts from the desired protein or polypeptide. For such applications, the method of the invention may provide a valuable alternative.

According to another preferred embodiment of the invention, the plant used to express the fusions of the invention is a starch producing plant, in particular a starch granule producing plant, and the protein or polypeptide expressed as part of said fusion according to the invention is an enzyme that can interact with starch or starch granules.

In this embodiment, after expression, the fusions preferably associate (either in vivo and/or during processing of the plant or plant material) with the starch (granules) via the one or more starch binding domains, after which the enzyme can interact with the starch (granule), for instance to convert, modify, alter, degrade or otherwise influence the starch, the starch granule or the (primary) structure or interactions thereof, resulting in (a plant or plant material that can be used to provide) a modified starch, i.e. a starch different from the starch naturally provided by the plant in at least one property thereof, and in particular in one or more of the properties "1–15" mentioned above.

In particular, in this aspect of the invention, the enzyme that can interact with the starch (granules) is an enzyme that does not occur naturally in (i.e. that is heterologous to) the original starch producing plant, but is for instance an enzyme derived from another plant or from a bacterium, fungus or (other) micro-organism as described above.

In this way, the invention can be used to provide a transformed plant that in vivo produces starches that are modified or altered (i.e. compared by the starch naturally produced by the original starch producing plant).

Therefore, yet another aspect of the invention relates to a method for providing a plant that contains or produces a modified starch and/or modified starch granules, comprising at least one step of:
a) transforming a starch producing plant, in particular a starch granules producing plant, with a genetic construct comprising at least one nucleotide sequence encoding an enzyme that can interact with starch and/or starch granules and at least one nucleotide sequence encoding a starch binding domain, such that said genetic construct is expressed in the plant or at least part thereof;
and optionally further comprising at least one step of:
b) providing descendants and/or further generations of the thus transformed plant, for instance via sexual or asexual multiplication, including crossing and/or other breeding techniques.

The invention further relates to the transformed plant producing modified starch (granules) thus obtained, or any descendant thereof, as well as cultivation material of said plant, including seed, tubers, stakes or seedlings.

This aspect of the invention also comprises a method for producing a modified starch and/or modified starch granules, comprising at least one step of:
a) cultivating a transformed plant that produces a modified starch and/or modified starch granules as described above, or a descendant thereof:
and optionally further comprises at least one step of:
b) isolating the modified starch or starch granules from the transformed plant or from any part thereof, such as its seeds, leaves, roots (including tuburous roots), tubers, stems, stalks, fruits, grains or flowers.

This aspect of the invention can in particular be used to provide potato, sweet potato, cassava and/or cereals such as maize, rice, wheat, and barley or other economically important crops that produce modified starches, i.e. in their tubers or seed, and such tubers or seeds containing modified starches form a further aspect of the invention. Another aspect of the invention resides in the modified starches thus obtained.

Alternatively, the invention may be used to provide starch granules that already contain one or more enzymes that can interact with starch, or plant material that contains such starch granules, i.e. attached to or incorporated within the starch granule via the one or more starch binding domains. After harvesting of the plant, plant material and/or starch granules, the enzymes may then be used in vitro to alter the properties of the starch (granule), to provide a modified starch.

For some applications, this embodiment may offer advantages over the in planta production of modified starches, for instance when specific conditions (such as temperature, pH optimum, the presence of certain co-factors, etc) are required for the starch converting activity of the enzyme, and/or when greater control over the enzymatic starch conversion(s) is desired. For instance, enzymes such as thermostable α-amylases and isoamylase may have an optimal temperature range for conversion that may not be achieved in planta (i.e. in the field); a suitable temperature can then be applied during subsequent processing of the harvested plant material.

In a sense, this embodiment combines features of the two aspects of the invention described above, in that on the one hand the invention is used to express/provide a "complex" of a starch (granule) and a fusion of a starch-converting enzyme and one or more starch binding domains; whereas on the other hand the enzymatic activity present in the complex thus obtained is then used—through post-harvesting modification(s)—to provide a modified starch.

Furthermore, and analogous to the above described interaction with the starch (granules), the enzymatic activity expressed as part of the fusion may also convert, modify, alter, degrade or otherwise influence any other compound(s) present within the plant, or any other part(s) or biological function of the plant. The enzymatic activity may also provide for the in vivo synthesis of one or more desired compounds within the plant, which may or may not occur naturally in the original plant.

Therefore, in its broadest sense, this embodiment of the invention may be used to provide the plant with (i.e. to express within the plant) any desired enzymatic and/or biosynthetic activity, in association with any starch (granules) present within the plant.

According to yet another embodiment of the invention, only a nucleotide sequence encoding one or more starch binding domains as described above is expressed in a plant. According to this embodiment, the starch binding domain, which usually will be heterologous to the plant, upon expression preferably associates with any starch (granules) present in the plant, so as to make the starch granules less accessable to or a less favorable substrate or one or more starch converting enzymes that are naturally present in the plant. More generally, the starch binding domains thus expressed may compete with the native starch converting enzymes present in the plant (i.e. for "space" on the starch granules), thus influencing the native starch conversion processes.

In this way, the method of the invention can be used to inhibit, alter, modify or otherwise influence one or more of the native biosynthetic pathways in the plant involved in the starch (granule) biosynthesis or metabolism, which again can result in (a plant producing) a modified starch. Also, the interaction of the starch binding domain(s) and the starch (granule) can again lead to an alteration or modification of the starch granule, such as changes in the (primary) structure, in the amylose content, in the crystallinity, etc.

Also, it should be noted that in this aspect of the invention, the nucleotide sequence may encode a single starch binding domain or two or more starch binding domains, which may be the same or different. Also, when such a nucleotide sequence encodes two or more (the same or different) starch binding domains, these domains may be fused or linked to each other, e.g. directly or via a suitable linker, including but not limited to those mentioned above for the fusions of the invention. The expression in a plant of such "linked" starch binding domains may for instance lead to starch (granules) which are crosslinked—e.g. to a larger extend compared to the native starch (granule)—by these linked starch binding domains, and/or may lead to one or more other alterations in the properties of the starch (granule), e.g. as mentioned above.

This aspect of the invention therefore generally comprises transforming a plant with a nucleotide sequence that codes for at least one starch binding domain, such that said starch binding domain is expressed in the plant, and preferably associated in vivo with any starch (granules) present in the plant or in any part thereof.

The nucleotide sequence is preferably in the form of a genetic construct as described above (but containing only the one or more sequences encoding a starch binding domain, optionally linked via a linker sequence, and any further elements known per se for such constructs as described above). Also, as more generally mentioned above, the 'starch binding domain' used in the may also include parts of the enzyme, protein or polypeptide from which the domain was derived, or may even be a full protein that has been made catalytically inactive, such as catalytically inactive GBSS I or the partially granule bound SSII (also sometimes referred to as gbSSII).

Therefore, yet another aspect of the invention relates to a method for providing a plant that contains or produces a modified starch and/or modified starch granules, comprising at least one step of:
a) transforming a starch producing plant, in particular a starch granules producing plant, with a genetic construct comprising at least one nucleotide sequence encoding a starch binding domain, such that said genetic construct is expressed in the plant or at least part thereof;
and optionally further comprising at least one step of:
b) providing descendants and/or further generations of the thus transformed plant, for instance via sexual or asexual multiplication, including crossing and/or other breeding techniques.

The invention further relates to the transformed plant producing modified starch (granules) thus obtained, or any descendant thereof, as well as cultivation material of said plant, including seed, tubers or seedlings.

This aspect of the invention also comprises a method for producing a modified starch and/or modified starch granules, comprising at least one step of:
a) cultivating a transformed plant that produces a modified starch and/or modified starch granules as described above, or a descendant thereof;
and optionally further comprises at least one step of:
b) isolating the modified starch or starch granules from the transformed plant or from any part thereof, such as its seeds, leaves, roots, tubers, fruits, etc.

Again, this aspect can in particular be used to provide provide potato, cassava, sweet potato, taro, sago, yam and/or cereals such as rice maize, wheat, barley or other economically important crops that produce modified starches, i.e. in their tubers or seed, and such tubers or seeds containing modified starches, from a further aspect of the invention.

Another aspect of the invention resides in the modified starches thus obtained, optionally in the form of a complex with one or more starch binding domains as obtained through expression of the above genetic construct.

Some non-limiting, preferred practical applications of the invention include:

Production of amylose-free starch, in particular amylose-free potato starch. Introduction of starch-binding domains, or any other protein binding to starch granules, may be used as an alternative for antisensing starch-converting enzymes, such as the GBSS I gene (or for mutating the GBSS I gene), to obtain amylose-free potato starch. In the amf mutant and the antisense GBSS I potato plants down-regulation of the amylose content occurs at the DNA and RNA level, respectively. In the SBD-expressing potato plants, reduction of the amylose content is based on competition between the expressed SBDs and GBSS I.

The inhibition of the starch-converting enzymes may be further manipulated (i.e. increased) by using tandem SBDs (instead of a single SBD) separated by an appropriate linker peptide. Depending on the affinity for raw starch of the SBD in comparison with GBSS I, a single SBD or a series of more than two SBDs may achieve an amylose-free potato starch.

Modification of starch fine structure in planta.

Modification of the fine structure of starch can be achieved in planta by concentrating certain enzymes, equipped with an SBD, in the granule, or at the granule surface. Thus, next to targeting polypeptides to the amyloplast, also targeting within the amyloplast can be achieved. For instance, the use of *Escherichia coli* glgB or a potato kinase (sometimes referred to as R1) fused with an SBD can increase the degree of branching and phosphorylation of the starch to a larger extent than the non-engineered proteins.

Generating (new) transgenic starches, which either may have different functional properties compared to the existing ones (such as increased freeze-thaw stability or altered theological properties), or which may be regarded as a better precursor for derivatization processes than the WT or amf potato starch.

Starch modification in vitro.

In addition to modification in planta, (further) modification of the fine structure of the starch may take place during or after processing of the harvested plant (material). By introducing a protein in or on the surface of the starch granule, a complex of the invention that serves as a kind of 'precursor starch' can be obtained, which can be converted to the starch of interest after extraction of the starch from the plant (material). Thus, in this embodiment, the actual (or full) modification of the starch may not or may only in part be achieved in planta. The advantage of this is that (further) modification of the starch can take place under more controlled, and/or more extreme conditions than encountered in the plant in vivo, and/or in the presence of compounds such as reactants or co-factors which are not present in the amyloplast.

As an example thereof, the introduction of an oxidase/dehydrogenase as a fusion with one or more starch binding domains can be mentioned, yielding a more reactive starch after appropriate incubation in vitro. In this way, the derivatized starch can be obtained in a much more environmentally friendly manner than when chemical methods were applied.

Starch granules with immobilized enzymes.

In this application, a foreign enzyme is introduced in or onto the starch granule, with the objective of using the granules as a carrier of enzymes. An enzyme of choice is fused to a SBD (with linker), and this fusion protein is incorporated into the starch granule during starch biosynthesis. Subsequently, these granules can be used to catalyze certain in vitro conversions in which reactants and products diffuse in and out of the granule. Such a procedure allows a simple separation of enzyme and products. In addition the enzyme can be re-used.

Specialty support for affinity chromatography.

In this application, a protein without a catalytic activity is introduced in or onto the starch granule during starch biosynthesis. The SBD can be fused to any kind of receptor, and the forth-coming starch can subsequently be used as a support for affinity chromatography, i.e. small molecules can be specifically absorbed from complex mixtures such as culture filtrates or plant extracts, and eluted after several wash steps.

Molecular pharming of industrial enzymes.

In this application the starch granule also serves as an affinity support, but in a different context. Industrially relevant enzymes are fused to a SBD (with linker), and can be produced in, for instance, the vacuole of plant cells. Upon disruption of the tissue, the enzymes are released from this compartment, and are able to contact the surface of granules released from the amyloplast. After washing, the fusion proteins may be eluted from the granules with a maltodextrin solution. It is also possible to release the enzyme (without SBD) with a highly specific protease.

Production of cross-linked starches or starch granules.

In this application, protein-carbohydrate interactions (SBD-starch) are combined with protein—protein interactions (for instance, a leucine 'zipper').

Two possible uses thereof are for instance in reinforcing the granule and/or in creating a stronger starch gel after the granules are gelatinized.

For reinforcing the granule, a leucine zipper domain may be flanked by one or two SBDs. The zipper domains can create a second network in the granule, which is connected to the first (starch) by the SBD(s). Possibly, the melting temperature of the granule can be changed in this way. Reinforcing the starch structure in this way may also be useful for providing complexes of the invention that can for example be used in high temperature conversions. (Mutant starches like maize amylose-extender starch may also be useful in this respect)

For creating a stronger starch gel after gelatinization, a zipper domain may be flanked by a SBD on one side and a Maltose Binding Protein or 'MBP' on the other. The zipper domain is anchored in the granule by a SBD. After gelatinization, the zipper domains are connected, and this new network is attached to the starch network by MBPs. Gels with new properties may be realized in this way. In this aspect, the thermostability of the MBP may be of importance.

The invention will now be further illustrated by means of the Experimental Part given hereinbelow, as well as the Figures, in which:

FIG. 1 shows the amino acid sequence for some minimal sequences for starch binding domains suitable for use in the invention; *B. circulans* (SEQ ID NO:1), *A. niger* (SEQ ID NO:2), *T. thermosulfurigenes* (SEQ ID NO:3), *B stearothermophilus* (SEQ ID NO:4).

FIG. 2 schematically shows some examples of genetic constructs according to the invention containing reporter genes and the vector pBIN19$_{PTT}$ used as the starting material for the construction of these genetic constructs.

EXPERIMENTAL PART

A. Introduction

Starch is an important storage material in many plants, such as potato, sweet potato, cassava, pea, yam, taro, sago and cereals such as maize, rice, and potato. It is deposited as crystalline granules which generally consist of two polysaccharides, amylose (generally 20–30%) and amylopectin (70–80%). Amylose is an essentially linear molecule which is composed of (1→4)-linked α-D-glucopyranosyl (α-D-Glcp) residues. Amylopectin is a highly branched molecule composed of a collection of α-(1→4)-glucan chains which are connected by α-(1→6)-linkages (the branch points). It is believed that branching occurs at regular intervals, in such a way that clusters of sidechains are formed. The sidechains can interact laterally with each other which is presumably the basis for the crystalline nature of the granule.

Current models explain granule growth by addition of single Glc residues to the non-reducing ends of a nascent amylopectin molecule, a reaction catalyzed by synthases. Once the glucan chains have reached a certain length, they are thought to be rearranged with the help of a number of enzymes such as branching enzyme (BE), debranching enzyme (R-enzyme), and presumably also disproportionating enzyme (D-enzyme). As far as is currently known, starch-producing plant species can possess several isoforms of starch synthases (GBSS I, GBSS Ib, gbSS II, SSS I, and SSS III; GB=granule-bound, gb=partially granule-bound, S=soluble) and BE (BE I, BE IIa, and BE IIb).

The major differences between the potato starch synthase isoforms are the length of the N-terminal extension, and the location of expression in the plant. For SSS III the N-terminal extension is 780 amino acids long, for gbSS II 275. The C-terminal part of these two enzymes, SSS I, and GBSS I is very similar. Three regions in particular, termed box I to III, are highly conserved. Box I contains the "KTGGL" motif, which is the putative ADP-glucose binding site. The function of the other boxes is unknown. GBSS I and gbSS II are expressed in stolon and tuber, SSS I only in leaf, and SSS III in both tuber and leaf. The amino acid sequence of potato BE I and BE II is highly conserved, except at the extremities of the protein. BE II has a flexible N-terminal extension of approximately 120 amino acids which is absent in BE I. BE I has a C-terminal extension of 110 amino acids which BE II lacks. Contrary to maize, only two isoforms of BE have been found in potato so far. It should be noted that BE I is much more abundant than BE II in potato tubers. In maize three isoforms have been reported (BE I, IIa, and IIb). The isoforms BE IIa and BE IIb of maize are very similar with respect to their amino acid sequence (except for the c. 50 N-terminal amino acids). However, these isoforms seem to be expressed in different tissues.

Although the primary structure of many synthases and BEs has been documented, this is not the case for the biochemical properties of these enzymes. Based on observations in certain mutant backgrounds, there is some evidence suggesting that each synthase plays a particular role in elongating sidechains of a specific length. Further, GBSS I is the only synthase involved in the synthesis of amylose. Next to (slightly) different catalytic properties, it is expected that the ability of synthases to bind to starch granules is determinative for their role in the biosynthesis process. GBSS I is found predominantly in the starch granule, whereas SSS III is found predominantly in the soluble phase. The gbSS II and SSS I seem to hold intermediate positions. The isoforms of BE seem to display a somewhat different mode of action. BE II prefers to transfer shorter glucan chains to an acceptor substrate than BE I. In addition, other properties of the BEs might determine their specific roles in the biosynthesis process. For instance, BE II seems to associate more strongly with starch granules than BE I. In fact, one might say that BE II is partially granule-bound (maybe gbBE would be a more appropriate name). It is unknown whether its starch-binding ability is mediated through the N-terminal extension (which is typical for BE II).

Over the years, the level of several of the synthase or BE isoforms has been down-regulated by mutation or antisense technology. This large amount of data suggests that decreasing the level of granule-bound enzymes has more severe consequences for the starch granule architecture than that of their soluble isoforms. The presence of GBSS I determines whether or not amylose is deposited in starch granules. Knocking out SSS III expression in potato leads to a different granule morphology (T-shaped cracks and clusters of small granules). However, starch content of the tubers, the granule size, and the ratio of amylopectin and amylose remain more or less unaltered. Inhibition of gbSS II expression in potato does not result in large changes in starch content, morphology or composition. However, mutation of the pea gbSS II gene can result in an altered granule morphology and amylopectin structure.

The impact of downregulating a particular synthase may be related to how much this isoform contributes to the total amount of synthase activity in the crop. However, this may be difficult to assess. BE I is the most abundant BE isoform in potato tuber, and it resides predominantly in the soluble phase. Antisensing the gene encoding this enzyme effectively removes the BE activity from the tuber juice, but surprisingly, the starch structure is not affected by this. However, decreasing the level of BE II protein (which is at least partially granule-bound) in potato tuber by antisense technology dramatically reduces the number of α-(1→6) branchpoints in the starch (and probably also the starch content of the tuber), and consequently the functional properties of the starch. The starch produced in this way shares some characteristics with the amylose-extender mutant in maize, in which the gene encoding BE IIb is inactivated.

According to the invention, soluble enzymes could be made granule-bound; and techniques can be provioded make other (non-)biosynthetic enzymes granule-bound.

Protein-carbohydrate interactions are not understood with respect to starch biosynthetic enzymes (or granule-boundness), but the ability to bind to crystalline particles is a common feature of many cellulose- or starch-degrading enzymes. In general, these enzymes are composed of two or more domains which are connected by linker peptides. One of these domains contains the catalytic function of the protein, whereas other domains are involved in anchoring the proteins to the water-insoluble polysaccharide matrix. The so-called binding-domains (BDs) are usually relatively small (30 to approximately 160 amino acids) compared to the catalytic domains (>200 amino acids). As a result of this, the 3D structures of a large number of BDs have been solved. These studies have provided a rather detailed picture of how a protein interacts with carbohydrates. Further, a number of candidate amino acid residues which are presumably involved in binding the polysaccharide could be indicated. In some cases the importance of these residues for binding was verified by site-directed mutagenesis experiments. The interaction of cellulose-binding domains (CBDs) with cellulose and of (raw) starch-binding domains (SBDs) with starch granules will be further discussed hereinbelow.

Unlike CBDs, the amino acid sequences of SBDs seem very well conserved among different enzymes (α-amylase, β-amylase, glucoamylase, cyclodextrin glycosyltransferase [CGTase], etc.), as well as among different species (*Aspergillus niger, Bacillus circulans, Streptomyces limosus, Clostridium thermosulfurogenes, Pseudomonas stutzeri, Klebsiella pneumoniae*, etc.). In analogy to CBD type I, II, III, and V, SBDs are rather rigid structures which are predominantly composed of β-strands. Based on their interaction with maltose or cyclodextrin, usually two separate sugar-binding sites (1 and 2) can be distinguished in SBDs, which contain two or three exposed aromatic amino acids. The structure of site 1 is better conserved among the different SBDs than that of site 2, and has presumably a higher affinity for ligands than site 2. It contains two easily accessible Trp residues, which more or less keep their orientation upon ligand binding. Site 2 is much longer than site 1 and contains two or three Tyr residues which are located on a rather flexible loop of the SBD. Upon binding, site 2 undergoes significant structural changes which may allow the SBD to interact with starch in various orientations. In CGTases the SBD is part of a complex structure which comprises 5 separate domains. In these enzymes, site 1 is on the outside of the protein, whereas site 2 is more buried in the protein structure forming part of a channel leading to the catalytic site of the enzyme. Site-directed mutagenesis of aromatic amino acid residues belonging to both site 1 and 2 suggest that site 1 is the actual (raw) starch binding site whereas site 2 is involved in guiding glucan chains to the catalytic site of the CGTase. It is not known whether site 2 also contributes to binding of starch granules.

Next to the SBDs, there are also proteins which only bind soluble α-glucans. An example of this is the maltodextrin-binding protein (MBP) from *Escherichia coli*. The amino acid residues that are involved in ligand binding are buried in the MBP structure. From the above, it can be seen that at least some the following factors may influence protein-carbohydrate interactions: (i) aromatic amino acids (often two or more) play a major role in these interactions; (ii) for binding crystalline structures these residues are positioned on an exposed face of the protein; (iii) for binding water-soluble molecules or amorphous structures these residues, or residues with a similar function are lining a groove, buried in the protein.

A number of enzymes involved in starch biosynthesis have been shown to associate with starch granules; one preferred subclass thereof according to the invention are the synthases. Reasons for this are the availability of several synthase genes and a mutant GBSS I (amf) potato plant (producing an amylose-free starch).

EXAMPLE I

Determining Factors Involved in the Granule-Boundness of GBSS I

WT, mutant and fusion proteins can be expressed in *E. coli* using a suitable expression system. Subsequently, the various enzymes can be purified, and their biochemical characteristics (activity, starch-binding) can be determined. Potato plants (both WT and amf background) can then be transformed with selected genes, based on the properties of their corresponding proteins. The forthcoming transgenic starch granules can then be analyzed for alterations in their size, morphology, and composition (including the fine structure of the polysaccharides if necessary). Thus, polymer production can be studied in planta with well-characterized proteins providing the essentials to understand why this polymer was made.

The amino acid sequence of GBSSI is determined in a manner known per se, for instance from the nucleotide sequence of an isolated GBSSI-encoding cDNA. Based on amino acid sequence alignments of various synthases a number of Trp or Tyr residues in the GBSSI sequence can be selected as candidates for the interaction with starch granules. These (and combinations of these) can be replaced by site-directed mutagenesis. The mutant proteins are then be purified and analyzed for a reduced starch-binding capacity.

Potato (amf background) is then transformed with mutant GBSS I with reduced affinity to determine whether amylose biosynthesis can be restored to a similar extent as with WT GBSS I.

Based on the above experiments, aromatic amino acids can be introduced at appropriate positions in glgA from *Bacillus subtilis*, to study whether this enzyme can be made granule-bound. Potato plants (amf background) can then be transformed with mutant glgA ('s) to study whether amylose biosynthesis can be restored. In this way the starch-binding site of GBSS I can be mapped. Alternatively, the Tyr residues involved in binding could be replaced by Trp residues in order to tailor a GBSS I with improved starch-binding characteristics (as Trp residues are known to bind with higher affinity than Tyr residues).

EXAMPLE II

Tailoring Granule-Boundness

Granule-boundness may be tailored by fusing a relatively small SBD (100 amino acids), such as the SBD of the CGTase from *Bacillus circulans*, to a ("soluble") protein of interest.

This protein used can for instance be a soluble starch synthase, in order to provide amf potato plants that can be used as a model system for studying the potential of "artificial" granule-boundness in planta (i.e. to determine whether amylose biosynthesis in an amf background can be restored by expression of a fusion of the invention). Different fusions can be made. Next to synthases equipped with one SBD, also synthases with a two SBDs can be expressed, optionally with variations in in the linker peptides connecting synthase and SBD(s). The fusion proteins can also be expressed in *E. coli*, and subsequently purified to investigate their biochemical properties (starch-binding, activity). Potato plants (amf background) can be transformed with selected fusion proteins to study whether amylose biosynthesis can be restored to a similar extent as with WT GBSS I.

In addition, WT potato plants can be transformed with a gene encoding a single SBD or a double SBD to determine the competition between GBSS I and SBD(s) in vivo. This may also serve as an alternative way to make an amylose-free potato starch.

In these experiments, transformation of WT potato plants with (double) SBDs will also show whether GBSS I and SBD bind to similar parts (or structures) in the starch granule (i.e whether GBSS I and SBD differ in their binding specificity). A different binding specificity would also provide the opportunity to target proteins to different parts of the starch granule, and also to use an inactive GBSS I (for instance obtained via genetical modification) as an alternative for a SBD in fusions. In addition, by making deletion mutants, different parts of GBSS I can be tested and used for their affinity for starch. (In this manner, alternative starch-binding domains could be obtained, with the same binding properties as GBSS I, but (much) of smaller size and and without catalytic activity.)

EXAMPLE III

Enzyme Fusions and Possible Applications

Three possible enzymes that can be equipped with an SBD by expression as a fusion of the invention are the *Escherichia coli* glycogen branching enzyme GLGB, the potato kinase R1, and a glucose oxidase/dehydrogenase. The former two have already been expressed in potato without a SBD. By expression of these proteins as a fusion of the invention, their impact on starch structure and functionality can be increased.

EXAMPLE III-1

Preparation of Extra Heavily Branched Amylopectin

In a previous investigation by Applicant, the amount of branching in starch polymers was increased by introducing a heterologous branching enzyme in both WT and amf potato plants. The outcome of these experiments was as follows. (i) In an amf background an additional 25% of branching of the amylopectin was obtained. (ii) In a WT background evidence was obtained that next to the extra branching of amylopectin, amylose disappears as such. (Assuming that amylose is synthesized downstream of amylopectin, this indicates that Glgb is (partially) granule-bound.)

Additional branching compared to these reference tests might be achieved when glgB is specifically targeted to (and thus concentrated at) the granule surface by equipping the enzyme with a SBD, i.e. by expressing it in planta as a fusion of the invention. In this way, with a fusion of the invention, possibly a larger increase in branching can be obtained (i.e. compared to transforming with glgB per se), to provide improved freeze-thaw stability of starch solutions.

EXAMPLE III-2

Phosphorylated Starch

Potato starch differs from many other starches in that it is more heavily phosphorylated. There is roughly one phosphate group to 700 Glc residues. Phosphorylation can occur at the C-6 (65%) or the C-3 position (35%) of Glc. The relatively large phosphate content gives potato tuber starch a number of unique properties such as the "peak viscosity" upon gelatinizing the granule, an anionic character, and possible anchors for derivatization.

Recently, an enzyme has been cloned which is presumably responsible for phosphorylation of starch. This kinase, further referred to as R1, cleaves ATP, and transfers a phosphate group to an unknown donor molecule. Phosphorylation of starch could be further increased by expressing a fusion of an SBD and R1 in planta, for instance in potato or cassava (heterologous expression).

EXAMPLE III-3

Oxidized Starch

Starch contains a large collection of hydroxyl groups (—[CH2]—OH), but these are not very reactive. Next to these, each starch polymer contains an aldehyde group (—[CH]=O) at the reducing terminus, which is much more reactive. Because the starch polymers are such large molecules, the number of reactive groups is too small to be a meaningful target for derivatization. One way to increase the number of aldehyde or carboxyl (—[COH]=O) groups is by oxidation. As an alternative to chemical oxidation procedures, oxidases or dehydrogenases can be used, i.e. by expression as a fusion according to the invention. This could already lead to (increased) oxidation in planta, but also, and preferably, an oxidative enzyme fused to an SBD is incorporated in a starch granule during granule biogenesis, and subsequently these granules are incubated in vitro under conditions (temperature, pH, co-factors) suitable to provide oxidation of the starch.

EXAMPLE IV

Constructs Containing Reporter Genes

Schematic representations of some non-limiting examples of constructs of the invention are shown in FIG. 2. Instead of the luciferase gene shown in FIG. 2, also another reporter gene such as (a sequence encoding a) beta-glucuronidase (GUS) can be used, or a sequence encoding the desired protein or polypeptide.

Briefly, the assembly of all constructs for potato transformation was started with the vector pBINI9$^{PTT}$ (FIG. 2), which already contained the tuber-specific GBSS I promoter, the amyloplast-targeting signal of potato GBSS 1, and the NOS terminator sequence (for legend see figure). The starch-binding modules SBD and GBSS were obtained by standard PCR using the cyclodextrin glycosyltransferase of *Bacillus circulans* and potato granule-bound starch synthase I as a template, respectively. The luciferase template (pLUK07/LUC) was obtained from the North Carolina State University. PCRs were performed in such a way that the appropriate restriction sites were introduced in the genes of interest. The relevant restriction sites are indicated in FIG. 2. An artificial linker sequence was designed, containing a BglII and an EcoRl restriction site at, respectively, the 5' and 3' end of the sequence. The amino acid sequence of the PT-rich linker peptide corresponds to "RSPTPTPT-TPTPTPTTPTPTPSTE" (SEQ ID NO:5). The correctness of the constructs was confirmed by DNA sequencing. The constructs were introduced in both WT and amylose-free potato plants using standard *Agrobacterium*-mediated transformation procedures. The constructs provide the opportunity (i) to investigate whether SBD and GBSS bind the granule at a different location; (ii) to compare the affinity of SBD, SBD$_2$ and GBSS for starch during granule biosynthesis; (iii) to verify the concept of targeting foreign catalytic activities to the starch granule during biosynthesis.

SBD and double SBD were also cloned into a pTrcHisB vector (Invitrogen) in order to express both proteins in *Escherichia coli*. In these constructs, a 6×HIS tag was fused to the N-terminus of the proteins, which facilitated purification of these proteins from culture filtrates. The purified proteins were used for two purposes. (i) They were used in a standard rabbit immunisation procedure to obtain polyclonal antibodies. The antibodies recognized the SBD proteins in blotting experiments. (ii) They were used for in vitro starch granule binding assays. In a typical experiment SBD or SBD$_2$ are adsorbed on to the granule surface. The proteins can be desorbed with maltose. The concentration of maltose at which the proteins are released from the surface is indicative for the strength of binding.

The transgenic tubers can be subjected to Northern blot analysis using similar procedures as described in Salehuzzaman et al. (1999) Plant Cell Environment 22, 1311–1318. Starch granules can be isolated by grinding the tuber tissue in the presence of 0.5% (w/v) Na$_2$S$_2$O$_5$, followed by 3 washing/centrifugation steps with 30 mM phosphate buffer pH7, and subsequently 3 washing/centrifugation steps with distilled water. The starch is then suspended in aceton, and air-dried. The starch can be subjected to Western blot analysis in essentially the same way as described in Salehuzzaman et al. [(1999) Plant Cell Environment 22, 1311–1318], using the polyclonal antibodies mentioned above. The structural features and/or physical properties of the starch can be further characterized by using (a selection of) the methods outlined below.

EXAMPLE V

Constructs Containing Genes that can Interact with Starch

In the constructs described in Example IV, the reporter gene may be replaced by a gene that can "interact with starch" as defined hereinbelow (e.g. by using in the protocol described in Example IV a nucleotide sequence encoding a gene that can interact with starch instead of the luciferase template.)

Examples of such genes may include, but are not limited to, a branching enzyme (e.g. from potato, pea, maize or *Escherichia coli*), an alpha-amylase (e.g. from *Aspergillus oryzae* or *Bacillus licheniformis*), pullulanase (e.g. from *Klebsiella aerogenes*, isoamylase (e.g from *Pseudomonas amyloderamosa*), amylomaltase (e.g. from *Bacillus*), sucrase (e.g. from *Leuconostoc mesenteroides* or *Streptococcus mutans*, a potato kinase (e.g. for adding phosphate groups to starch), an oxidase (e.g. glucose oxidase from *Aspergillus niger* or a dehydrogenase (e.g. glucose dehydrogenase from *Acinetobacter calcoaceticus* or *gluconobacter*).

The constructs thus obtained can be transformed into a starch-producing plant, such as potato, e.g. using *Agrobacterium* as described in Example IV.

The transformed potato plants thus obtained can be used to produce tubers that contain starch (granules) with altered properties compared to the starch (granule) natively produced by the potato plant.

The invention claimed is:

1. A genetic construct comprising (a) a first nucleotide sequence encoding an enzyme that interacts with starch or starch granules, (b) a second nucleotide sequence encoding a bacterial starch binding domain, (c) a promoter that directs expression in a plant to a seed, leaf, root, tuber, stem, stalk, fruit, grain, and/or flower of a fusion protein comprising the enzyme and the bacterial starch binding domain, and (d) a region encoding a linker sequence, wherein the linker sequence is present in the fusion protein between the enzyme and the bacterial starch binding domain, wherein the construct is suitable for transforming a plant, and wherein the plant transformed with the construct expresses a fusion protein comprising the enzyme, the linker and the bacterial starch binding domain.

2. The genetic construct of claim 1, wherein the enzyme is a potato granule bound starch synthase I (GBSS1).

3. The genetic construct of claim 1, wherein the bacterial starch binding domain is a starch binding domain of a cyclodextrin glycosyltransferase (CGTase) from Bacillus circulans.

4. The genetic construct of claim 1, further comprising a region encoding a signal sequence, wherein the signal sequence causes the fusion protein to be directed to a starch containing cell.

5. The genetic construct of claim 4, wherein the signal sequence is the potato GBSS1 signal sequence.

6. A plant transformed with the genetic construct of claim 1, or a descendent of the plant, wherein the descendent of the plant contains the genetic construct and expresses the fusion protein.

7. The plant of claim 6, wherein the fusion protein is expressed in a tuber of the plant.

8. The plant of claim 6, wherein the fusion protein is expressed in a flower of the plant.

9. The plant of claim 6, wherein the plant is selected from the group consisting of potato, sweet potato, cassava, pea, taro, sago, yam, banana, rice, maize, wheat and barley.

10. A seed, tuber, seedling, or other cultivating material from the plant of claim 6, wherein the seed, tuber, seedling, or other cultivating material contains the genetic construct and expresses the fusion protein.

11. A method for expressing a fusion protein in a plant, the method comprising the steps of transforming the plant with the genetic construct of claim 2 and allowing the plant transformed with the genetic construct to express the fusion protein, thereby expressing the fusion protein in the plant.

12. The method of claim 11, wherein the plant is selected from the group consisting of potato, sweet potato, cassava, pea, taro, sago, yam, banana, rice, maize, wheat and barley.

13. A method for increasing the affinity for starch and/or starch granules of an enzyme that can interact with starch and/or starch granules in a plant, the method comprising the steps of transforming a plant with a genetic construct comprising a nucleotide sequence that encodes a fusion protein, wherein the fusion protein comprises the enzyme, and at least one bacterial starch binding domain, and a linker present in the fusion protein between the enzyme and the bacterial starch binding domain, and allowing the plant to express the fusion protein, thereby increasing the affinity of the enzyme for starch and/or starch granules.

14. A plant expressing the fusion protein of claim 13.

15. A seed, tuber, seedling, or other cultivating material from the plant of claim 14, wherein the seed, tuber, seedling, or other cultivating material expresses the fusion protein.

* * * * *

UNITED STATES PATENT AND TRADEMARK OFFICE
CERTIFICATE OF CORRECTION

| | | |
|---|---|---|
| PATENT NO. | : 7,135,619 B1 | Page 1 of 1 |
| APPLICATION NO. | : 10/009876 | |
| DATED | : November 14, 2006 | |
| INVENTOR(S) | : Richard Gerardus F. Visser and Jean-Paul Vincken | |

It is certified that error appears in the above-identified patent and that said Letters Patent is hereby corrected as shown below:

Title page

Item (22), PCT Filed, "Jun. 11, 1999" should read --Jun. 13, 2000--.

Signed and Sealed this

Twenty-eighth Day of August, 2007

JON W. DUDAS
*Director of the United States Patent and Trademark Office*